(12) United States Patent
Noordam et al.

(10) Patent No.: US 10,947,573 B2
(45) Date of Patent: *Mar. 16, 2021

(54) PROCESS FOR ENZYMATIC HYDROLYSIS OF LIGNOCELLULOSIC MATERIAL AND FERMENTATION OF SUGARS

(71) Applicant: DSM IP ASSETS B.V., Heerlen (NL)

(72) Inventors: Bertus Noordam, Echt (NL); Loes Elizabeth Bevers, Echt (NL); Rudy Francois Maria Jozef Parton, Echt (NL); Michael Petrus Jozef Berkhout, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/408,062

(22) Filed: May 9, 2019

(65) Prior Publication Data

US 2020/0270659 A1    Aug. 27, 2020

Related U.S. Application Data

(63) Continuation of application No. 15/307,241, filed as application No. PCT/EP2015/059316 on Apr. 29, 2015, now Pat. No. 10,337,040.

(30) Foreign Application Priority Data

| Apr. 30, 2014 | (EP) | ................................ | 14166538 |
| Apr. 30, 2014 | (EP) | ................................ | 14166539 |
| Apr. 30, 2014 | (EP) | ................................ | 14166545 |
| May 7, 2014 | (EP) | ................................ | 14167284 |
| May 8, 2014 | (EP) | ................................ | 14167483 |

(51) Int. Cl.
| C12P 19/02 | (2006.01) |
| C13K 1/02 | (2006.01) |
| D21C 3/26 | (2006.01) |
| C13K 13/00 | (2006.01) |
| C12P 19/14 | (2006.01) |

(52) U.S. Cl.
CPC .............. *C12P 19/02* (2013.01); *C12P 19/14* (2013.01); *C13K 1/02* (2013.01); *C13K 13/00* (2013.01); *C13K 13/002* (2013.01); *D21C 3/26* (2013.01); *C12P 2203/00* (2013.01); *Y02E 50/10* (2013.01)

(58) Field of Classification Search
None
See application file for complete search history.

(56) References Cited

U.S. PATENT DOCUMENTS

| 9,957,528 B2 | 5/2018 | Noordam et al. |
| 9,982,280 B2 | 5/2018 | Noordam et al. |
| 10,087,475 B2 | 10/2018 | Noordam et al. |
| 10,144,939 B2 | 12/2018 | Noordam et al. |
| 10,337,040 B2 | 7/2019 | Noordam et al. |
| 10,557,157 B2 | 2/2020 | Noordam |
| 10,597,689 B2 | 3/2020 | Noordam et al. |
| 2004/0147621 A1 | 7/2004 | Font-Freide et al. |
| 2009/0035826 A1 | 2/2009 | Tolan et al. |
| 2010/0159535 A1 | 6/2010 | Xu et al. |
| 2010/0304437 A1 | 12/2010 | Garner et al. |
| 2011/0076725 A1 | 3/2011 | Yang et al. |
| 2012/0114797 A1 | 5/2012 | Perkins et al. |
| 2012/0183993 A1 | 7/2012 | Smits et al. |
| 2015/0203885 A1 | 7/2015 | Noordam |
| 2015/0315622 A1 | 11/2015 | Frickmann et al. |

(Continued)

FOREIGN PATENT DOCUMENTS

| AU | 2001268603 B2 | 11/2006 |
| CN | 102191299 A | 9/2011 |

(Continued)

OTHER PUBLICATIONS

Notice of Opposition of European Patent Application No. 13792865.1 dated Apr. 7, 2020.
Jagani, Hitesh et al., "An OVerview of Fermenter and the Design Considerations to Enhance Its Productivity", Pharmacologyonline, 2010, pp. 261-301, vol. 1.
Reiner, Karen, "Catalase Test Protocol", American Society for Microbiology, Nov. 11, 2010.
Villadsen, John et al., "Bioreaction Engineering Principles", Third Edition, 2011, pp. 443-445.

(Continued)

*Primary Examiner* — Paul J Holland
(74) *Attorney, Agent, or Firm* — McBee Moore & Vanik IP, LLC

(57) ABSTRACT

The invention relates to a process for the preparation of a fermentation product from lignocellulosic material, comprising the following steps:
a) optionally, pretreatment of the lignocellulosic material,
b) optionally, washing of the optionally pretreated lignocellulosic material,
c) enzymatic hydrolysis of the optionally washed and/or optionally pretreated lignocellulosic material using an enzyme composition comprising at least two cellulases and whereby the enzyme composition at least comprises LPMO, and optionally purifying the hydrolysed lignocellulosic material,
d) fermentation of the hydrolysed lignocellulosic material to produce a fermentation product, and
e) optionally, recovery of a fermentation product,
wherein the amounts of formed hydrolysed oxidation products at the end of the enzymatic hydrolysis by the oxidation by LPMO of the lignocellulosic material containing cellulose and/or cello-oligosaccharides is kept between 3 to 80 g/kg glucan present in the lignocellulosic material by adding a suitable amount of oxygen after the pre-treatment and before and/or during the enzymatic hydrolysis to the lignocellulosic material, preferably the formed hydrolysed oxidation product is gluconic acid, an aldonic acid and/or geminal diol, more preferably the hydrolysed oxidation product is gluconic acid.

17 Claims, No Drawings

(56) References Cited

U.S. PATENT DOCUMENTS

| | | | |
|---|---|---|---|
| 2018/0073048 A1 | 3/2018 | Noordam | |
| 2019/0093137 A1 | 3/2019 | Smits et al. | |

FOREIGN PATENT DOCUMENTS

| | | | |
|---|---|---|---|
| CN | 102325889 | A | 1/2012 |
| CN | 102459582 | A | 5/2012 |
| CN | 103314111 | A | 9/2013 |
| EP | 0058426 | A1 | 8/1982 |
| EP | 1735454 | A2 | 12/2006 |
| EP | 3234168 | A1 | 10/2017 |
| EP | 2917359 | B1 | 7/2019 |
| JP | 2008/521396 | A | 6/2008 |
| JP | 2010/531668 | A | 9/2010 |
| JP | 2012/504937 | A | 3/2012 |
| WO | 94/03634 | A1 | 2/1994 |
| WO | 01/60752 | A1 | 8/2001 |
| WO | 2005/100582 | A2 | 10/2005 |
| WO | 2006/056838 | A1 | 6/2006 |
| WO | 2007/091231 | A1 | 8/2007 |
| WO | 2008/008793 | A2 | 1/2008 |
| WO | 2009/003167 | A1 | 12/2008 |
| WO | 2009/046538 | A1 | 4/2009 |
| WO | 2009/055793 | A1 | 4/2009 |
| WO | 2010/138754 | A1 | 2/2010 |
| WO | 2010/080407 | A2 | 7/2010 |
| WO | 2011/000949 | A1 | 1/2011 |
| WO | 2011/042437 | A3 | 4/2011 |
| WO | 2012019151 | A1 | 2/2012 |
| WO | 2012/061517 | A1 | 5/2012 |
| WO | 2012/088429 | A2 | 6/2012 |
| WO | 2012130120 | A1 | 10/2012 |
| WO | 2012/149275 | A1 | 11/2012 |
| WO | 2013/028701 | A1 | 2/2013 |
| WO | 2014/072390 | A1 | 5/2014 |
| WO | 2014/072392 | A1 | 5/2014 |
| WO | 2014/072393 | A1 | 5/2014 |
| WO | 2014130812 | A1 | 8/2014 |
| WO | 2015/075277 | A1 | 5/2015 |
| WO | 2016/096971 | A1 | 6/2016 |

OTHER PUBLICATIONS

Leggio, Leila Lo et al., "A Structural Overview of GH61 Proteins—Fungal Cellulose Degrading Polysaccharide Monooxygenases", Computational and Structural Biotechnology Journal, Sep. 2012, vol. 2, No, 3.
Beeson, William T. et al., "Oxidative Cleavage of Cellulose by Fungal Copper-Dependent Polysaccharide Monooxygenases", Jounral of the American Chemical Society, Dec. 20, 2011, pp. 890-892, Vol, 134.
International Search Report of International Patent Application No. PCT/EP2013/073250 dated Jan. 8, 2014.
Bey et al., "Cello-oligosaccharide oxidation reveals differences between two lytic polysaccharide monooxygenases (family GH61) from Podospora anserina", Applied and Environmental Microbiology, vol. 79, Nov. 2, 2012 (Nov. 2, 2012), pp. 488-496, XP008160285.
Kostylev et al., "Synergistic Interactions in Cellulose Hydrolysis", Biofuels, vol. 3, Jan. 2012 (Jan. 2012), pp. 61-70, XP002693861.
Horn et al., "Novel Enzymes for the Degradation of Cellulose", Biotechnology for Biofuels, vol. 5, Jul. 2, 2012 (Jul. 2, 2012), pp. 45(1)-56 (12), XP021122735.
Viikari et al., "Lignocellulosic ethanol: From science to industry", Elsevier, SciVerse ScienceDirect, Biomass and Bioenergy 46 (2012) pp. 13-24, XP-002718612.
Deng et al., "Influence of culture aeration on the cellulase activity of Thermobifida fusca", Appl Microbial Biotechnol (2010), Biotechnological Products and Process Engineering, pp. 965-974, XP19778511.
Hu et al., "The synergistic action of accessory enzymes enhances the hydrolytic potential of a "cellulase mixture" but is highly sustrate specific", Biotechnology for Biofuels 2013, 6:112, XP21158122A: pp. 1-12.

Kumar et al., "Recent Advances in Production of Bioethanol from Lignocellulosic Biomass." Chem. Eng. Technol. (2009) 32(4) 517-526.
Badger, "Ethanol From Cellulose: A General Review." Reprinted from: Trends in new crops and new uses. 2002.
Cannella et al., "Production and effect of aldonic acids during enzymatic hydrolysis of lignocellulose at high dry matter content." Biotechnology for Biofuels 2012, 5:26.
Canella et al., "Do New Cellulolytic Enzyme Preparations Affect the Industrial Strategies for High Solids Lignocellulosic Ethanol Production?" XP-002721360. Biotechnology and Bioengineering 2014, 111:1.
Levasseur et al., "Expansion of the enzymatic repertoire of the CAZy database to integrate auxiliary redox enzymes." Biotechnology for Biofuels 2013, 6:41.
Ioelovich et al., "Study of Enzymatic Hydrolysis of Pretreated Biomass at Increased Solids Loading." Bio Resources (2012), 7(4), 4672-4682.
Sweeney, Matt D. et al., "Biomass Converting Enzymes as Industrial Biocatalysts for Fuels and Chemicals: Recent Developments", Catalysts, Apr. 12, 2012, pp. 244-263.
Quinlan, R. Jason et al., "Insights into the Oxidative Degradation of Cellulose by a Copper Metalloenzyme that Exploits Biomass Components", PNAS, Sep. 13, 2011, pp. 15079-15084, vol. 108, No. 37.
Phillips et al., "Cellobiose Dehydrogenase and a Copper-Dependent Polysaccharide Monooxygenase Potentiate Cellulose Degradation by Neurospora crassa" American Chemical Society Chemical Biology, vol. 6, No. 12, pp. 1399-1406 (and supplement) electronically published Oct. 17, 2011.
International Search Report of International Patent Application No. PCT/EP2013/073255 dated Jan. 23, 2014.
International Search Report of International Patent Application No. PCT/EP2013/073253 dated Mar. 21, 2014.
International Search Report of International Patent Application No. PCT/EP2015/059317 dated Jul. 20, 2015.
International Search Report of International Patent Application No. PCT/EP2015/051839 dated Apr. 28, 2016.
Podkaminer, Kara K et al., "Ethanol and Anaerobic Conditions Reversibly Inhibit Commercial Cellulase Activity in Thermophilic Simultaneous Saccharification and Fermentation (tSSF)", Biotechnology for Biofuels, Jun. 15, 2012, vol. 5, No. 1, Biomed Central Ltd, GB.
Kumar, Manoj, "Development of a commercial enzyme system for lignocellulosic biomass saccharification", Final Technical Report, DSM Innovation Inc., 2012, pp. 1-23, DE-FC3608GO18079.
Li, Xin et al., "Cellobionic acid utilization: from Neurospora crassa to Saccharomyces cerevisiae", Biotechnology for Biofuels, 2015, pp. 1-9, vol. 8, No. 120.
Acknowledgment of receipt—Opposition proceedings in relation to EP 13792865.1 dated Mar. 31, 2020.
Communication of notices of opposition (R.79(1) EPC) in relation to EP 13792865.1 dated Jun. 17, 2020.
Response to opposition in relation to EP 13792865.1 dated Oct. 21, 2020.
Acknowledgment of receipt, consolidated list of cited opposition documents, and letter accompanying subsequently filed items in relation to EP 13792865.1 dated Oct. 21, 2020.
Brief communication—opposition proceedings in relation to EP 13792865.1 dated Oct. 27, 2020.
Halliwell, Barry et al., "Biologically relevant metal ion-dependent hydroxyl radical generation—An update", FEBS Jul. 1992, pp. 108-112, vol. 307, No. 1.
Bissaro, Bastien et al., "Oxidative cleavage of polysaccharides by monocopper enzymes depends on H2O2", Nature Chemical Biology, Oct. 2017, vol. 13.
Yang, Bin et al., "BSA Treatment to Enhance Enzymatic Hydrolysis of Cellulose in Lignin Containing Substrates", Biotechnology and Bioengineering, Jul. 5, 2006, pp. 611-617, vol. 94, No. 4.
European Patent Application No. 13184702, filed Sep. 17, 2013 (corresponds to WO 2014/072390A1—previously cited).
European Patent Application No. 13176500, filed Jul. 15, 2013 (corresponds to WO 2014/072390A1—previously cited).

(56) References Cited

OTHER PUBLICATIONS

European Patent Application No. 13174656, filed Jul. 2, 2013 (corresponds to WO 2014/072390A1—previously cited).
European Patent Application No. 12191957, filed Nov. 9, 2012 (corresponds to WO 2014/02390A1—previously cited).
Notice of Opposition of European Patent Application No. 13789275.8 dated Oct. 19, 2020.
Declaration of Magnus Wiman dated Oct. 9, 2020.

PROCESS FOR ENZYMATIC HYDROLYSIS OF LIGNOCELLULOSIC MATERIAL AND FERMENTATION OF SUGARS

CROSS-REFERENCE TO RELATED APPLICATIONS

This application is a continuation of U.S. patent application Ser. No. 15/307,241, filed 27 Oct. 2016, which is a National Stage entry of International Application No. PCT/EP2015/059316, filed 29 Apr. 2015, which claims priority to European Patent Application Nos. 14167483.8, filed 8 May 2014, 14167284.0, filed 7 May 2014, and 14166545.5, 14166539.8, and 14166538.0, all filed 30 Apr. 2014. The disclosure of the priority applications are incorporated in their entirety herein by reference.

BACKGROUND OF THE INVENTION

Field of the Invention

The invention relates to a process for the enzymatic hydrolysis of lignocellulosic material and fermentation of sugars.

Description of Related Art

Lignocellulosic plant material, herein also called feedstock, is a renewable source of energy in the form of sugars that can be converted into valuable products e.g. sugars or biofuel, such as bioethanol. During this process, (ligno- or hemi)cellulose present in the feedstock, such as wheat straw, corn stover, rice hulls, etc., is converted into reducing sugars by (hemi)cellulolytic enzymes, which then are optionally converted into valuable products such as ethanol by microorganisms like yeast, bacteria and fungi.

Since the (hemi)cellulose is crystalline and entrapped in a network of lignin the conversion into reducing sugars is in general slow and incomplete. Typically, enzymatic hydrolysis of untreated feedstock yields sugars <20% of theoretical quantity. By applying a chemical and thermo-physical pretreatment, the (hemi)cellulose is more accessible for the (hemi)cellulolytic enzymes and thus conversions go faster and at higher yields.

A typical ethanol yield from glucose, derived from pretreated corn stover, is 40 gallons of ethanol per 1000 kg of dry corn stover (Badger P., Ethanol from cellulose: a general review, Trends in new crops and new uses, 2002, J. Janick and A. Whipkey (eds.) ASHS Press, Alexandria, Va.) or 0.3 g ethanol per g feedstock. The maximum yield of ethanol on cellulose base is approximately 90%.

Cellulolytic enzymes—most of them are produced by species like *Trichoderma, Humicola* and *Aspergillus*—are commercially used to convert pretreated feedstock into a mash containing insoluble (hemi)cellulose, reducing sugars made thereof, and lignin. Thermostable cellulolytic enzymes derived from *Rasamsonia*, have been used for degrading lignocellulosic feedstock and these enzymes are known for their thermostability, see WO 2007/091231. The produced mash is used in a fermentation during which the reducing sugars are converted into yeast biomass (cells), carbon dioxide and ethanol. The ethanol produced in this way is called bioethanol.

The common production of sugars from pretreated lignocellulosic feedstock, the hydrolysis also called liquefaction, presaccharification or saccharification, typically takes place during a process lasting 6 to 168 hours (Kumar S., Chem. Eng. Technol. 32 (2009) 517-526) under elevated temperatures of 45 to 50° C. and non-sterile conditions. During this hydrolysis, the cellulose present is partly (typically 30 to 95%, dependable on enzyme activity and hydrolysis conditions) converted into reducing sugars. In case of inhibition of enzymes by compounds present in the pretreated feedstock and by released sugars and to minimize thermal inactivation, this period of elevated temperature is minimized as much as possible.

The fermentation following the hydrolysis takes place in a separate preferably anaerobic process step, either in the same or in a different vessel, in which temperature is adjusted to 30 to 33° C. (mesophilic process) to accommodate growth and ethanol production by microbial biomass, commonly yeasts. During this fermentation process, the remaining (hemi)cellulosic material is converted into reducing sugars by the enzymes already present from the hydrolysis step, while microbial biomass and ethanol are produced. The fermentation is finished once (hemi)cellulosic material is converted into fermentable sugars and all fermentable sugars are converted into ethanol, carbon dioxide and microbial cells. This may take up to 6 days. In general the overall process time of hydrolysis and fermentation may amount up to 13 days.

The so-obtained fermented mash consists of non-fermentable sugars, non-hydrolysable (hemi)cellulosic material, lignin, microbial cells (most common yeast cells), water, ethanol, dissolved carbon dioxide. During the successive steps, ethanol is distilled from the mash and further purified. The remaining solid suspension is dried and used as, for instance, burning fuel, fertilizer or cattle feed.

WO 2010/080407 suggests treating cellulosic material with a cellulase composition under anaerobic conditions. Removal or exclusion of reactive oxygen species may improve the performance of cellulose-hydrolyzing enzyme systems. Hydrolysis of cellulosic material, e.g. lignocellulose, by an enzyme composition can be reduced by oxidative damage to components of the enzyme composition and/or oxidation of the cellulosic material by, for example, molecular oxygen.

WO 2009/046538 discloses a method for treating lignocellulosic feedstock plant materials to release fermentable sugars using an enzymatic hydrolysis process for treating the materials performed under vacuum and producing a sugar rich process stream comprising reduced amounts of volatile sugar/fermentation inhibiting compounds such as furfural and acetic acid. Apart from removing volatile inhibitory compounds, other compounds and/or molecules that are also removed include nitrogen, oxygen, argon and carbon dioxide.

With each batch of feedstock, enzymes are added to maximize the yield and rate of fermentable sugars released from the pretreated lignocellulosic feedstock during the given process time. In general, costs for enzymes production, feedstock to ethanol yields and investments are major cost factors in the overall production costs (Kumar S., Chem. Eng. Technol. 32 (2009) 517-526). Thus far, cost of enzyme usage reduction is achieved by applying enzyme products from a single or from multiple microbial sources (WO 2008/008793) with broader and/or higher (specific) hydrolytic activity which use aims at a lower enzyme need, faster conversion rates and/or a higher conversion yields and thus at overall lower bioethanol production costs. This requires large investments in research and development of these enzyme products. In case of an enzyme product composed of enzymes from multiple microbial sources, large capital investments are needed for production of each single enzyme compound.

It is therefore desirable to improve the above process involving hydrolysis and fermentation.

SUMMARY

An object of the invention is therefore to provide a process in which the hydrolysis step is conducted at improved conditions. Another object of the invention is to provide a process involving hydrolysis having a reduced process time. Further object of the invention is to provide a process, wherein the dosage of enzyme may be reduced and at the same time output of useful hydrolysis product is maintained at the same level or even increased. Another object is to provide a process involving hydrolysis, wherein the process conditions of the hydrolysis are optimized. A still further object of the invention is to provide a process involving hydrolysis, wherein the output of useful hydrolysis product is increased using the same enzyme dosage. One or more of these objects are attained according to the invention.

The present invention provides a process for the preparation of a sugar product from lignocellulosic material, comprising the following steps:
  a) optionally, pretreatment of the lignocellulosic material,
  b) optionally, washing of the optionally pretreated lignocellulosic material,
  c) enzymatic hydrolysis of the optionally washed and/or optionally pretreated lignocellulosic material using an enzyme composition comprising at least two cellulases and whereby the enzyme composition at least comprises LPMO, and
  d) optionally, recovery of a glucose-containing composition,
wherein the amount of formed gluconic acid at the end of the enzymatic hydrolysis by the oxidation by LPMO of the lignocellulosic material containing cellulose and/or cello-oligosaccharides is kept between 3 to 80 g/kg glucan present in the lignocellulosic material by adding a suitable amount of oxygen after the pretreatment and before and/or during the enzymatic hydrolysis to the lignocellulosic material.

Furthermore the present invention provides a process for the preparation of a fermentation product from lignocellulosic material, comprising the following steps:
  a) optionally, pretreatment of the lignocellulosic material,
  b) optionally, washing of the optionally pretreated lignocellulosic material,
  c) enzymatic hydrolysis of the optionally washed and/or optionally pretreated lignocellulosic material using an enzyme composition comprising at least two cellulases and whereby the enzyme composition at least comprises LPMO, and optionally purifying the hydrolysed lignocellulosic material,
  d) fermentation of the hydrolysed lignocellulosic material to produce a fermentation product, and
  e) optionally, recovery of a fermentation product,
wherein the amount of formed gluconic acid at the end of the enzymatic hydrolysis by the oxidation by LPMO of the lignocellulosic material containing cellulose and/or cello-oligosaccharides is kept between 3 to 80 g/kg glucan present in the lignocellulosic material by adding a suitable amount of oxygen after the pretreatment and before and/or during the enzymatic hydrolysis to the lignocellulosic material.

Oxidation by LPMO of the lignocellulosic material results in oxidised polysaccharides which during the hydrolysis are hydrolysed into amongst others glucose and oxidised glucose units such as gluconic acid or diol. In general, 1 molecule oxygen ($O_2$) gives one mol oxidation product. Oxygen can also be taken up by the feedstock (e.g. lignin).

Preferably, the oxygen is added during the enzymatic hydrolysis step c).

In a preferred embodiment the oxygen is added in the form of (gaseous) bubbles.

Surprisingly, according to the invention by the addition of oxygen it is possible to attain many process advantages, including optimal temperature conditions, reduced process time, reduced dosage of enzyme, re-use of enzymes, higher yields and other process optimizations, resulting in reduced costs.

In one embodiment of this process the fermentation time is 5 to 120 hours. In an embodiment the stable enzyme composition used retains activity for 30 hours or more. According to a further embodiment the hydrolysis is preferably conducted at a temperature of 45° C. or more, more preferably at a temperature of 50° C. or more and still more preferably at a temperature of 55° C. or more. In a preferred embodiment the enzyme composition is derived from a fungus, preferably a microorganism of the genus *Rasamsonia* or the enzyme composition comprises a fungal enzyme, preferably a *Rasamsonia* enzyme. The process of the invention will be illustrated in more detail below.

DETAILED DESCRIPTION OF A PREFERRED EMBODIMENT

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. The articles "a" and "an" are used herein to refer to one or to more than one (i.e. to one or at least one) of the grammatical object of the article. By way of example, "an element" may mean one element or more than one element.

In the context of the present invention "improved", "increased", "reduced" is used to indicate that the present invention shows an advantage compared to the same situation, process or process conditions except that no extra oxygen is added. Within the context of the present invention "measured under the same conditions" or "analysed under the same conditions" etc. means that the process of the invention and the same process without addition of oxygen are performed under the same conditions (except the oxygen addition) and that the results of the present process, if compared to the process without oxygen addition, are measured using the same conditions, preferably by using the same assay and/or methodology, more preferably within the same or parallel experiment. Conditions of the hydrolysis are an example of such conditions.

In prior art it is suggested to improve the hydrolysis of cellulolytic material by using anaerobic (WO 2010/080407) or vacuum (WO 2009/046538) conditions during the enzymatic hydrolysis. In the processes of both documents the oxygen level was decreased. It has now surprisingly been found that the hydrolysis of the present invention shows results in an improved reaction product that gives higher amounts of (reduced) sugar products and/or desired fermentation products in the fermentation following the hydrolysis as compared to a process wherein no oxygen is added. In general, an increase of the glucose conversion is observed of 5 to 15 w/w %.

Oxygen can be added in several ways. For example, oxygen can be added as oxygen gas, oxygen-enriched gas such as oxygen-enriched air or air. Oxygen can be added continuously or discontinuously. By oxygen "is added" is meant that oxygen is added to the liquid phase (comprising the lignocellulosic material) in the hydrolysis reactor and not that oxygen is present in the headspace in the reactor above the liquid phase, whereby the oxygen has to diffuse from the headspace to the liquid phase. Preferably, oxygen is added or generated in the liquid phase (comprising the lignocellulosic material) in the hydrolysis reactor. So preferably, the oxygen is added as bubbles, most preferably as small bubbles. In an embodiment the bubbles have a diameter of at least 0.5 mm, at least 1 mm, at least 1.5 mm, at least 2 mm, at least 2.5 mm, at least 3 mm, at least 3.5 mm, at least 4 mm, at least 4.5 mm, at least 5 mm. In an embodiment the bubbles have a diameter of between 0.5 mm and 500 mm, preferably between 0.5 mm and 400 mm, between 0.5 mm and 300 mm, between 0.5 mm and 200 mm, between 0.5 mm and 100 mm.

The inventors pose the hypothesis that in the (enzymatic) hydrolysis (step) amorphous and crystalline polysaccharides or cellulose are hydrolysed to sugars such as glucose. Amorphous polysaccharides are for example converted to oligosaccharides by endogluconases, whereafter the oligosaccharides can be converted by cellobiohydrolase (CBH) and beta-glucosidase (BG) to glucose. The conversion of the crystalline polysaccharides may occur in parallel or sequential and continue even when most of the amorphous polysaccharides are hydrolysed. According to the present hypothesis especially the addition of oxygen in combination with LPMO is beneficial during the hydrolysis of the crystalline polysaccharides for example in the degradation of the polysaccharides into oligosaccharides. Therefore, the addition of oxygen is very useful especially in the phase wherein crystalline polysaccharides are converted by enzymes. Outside this phase, no addition of oxygen or adding less oxygen may be more efficient. This hypothesis is only given as possible explanation of the effect noticed by the inventors and the present invention does not fall or stand with the correctness of this theory.

The crystalline glucan structure can be opened by a lytic polysaccharide monooxygenase (LPMO). This type of enzyme opens up the structure by oxidizing the glycosidic bonds and making it accessible for the other cellulolytic enzymes for further hydrolyzing the oligosaccharides into glucose.

Most known LPMO's form aldonic acids, i.e. products oxidized at the C1 position of the terminal sugar at the cleavage site. This oxidized glucose unit is released as gluconic acid during hydrolysis. In addition, oxidation of the C4 and C6 of the non-reducing glucose unit at the cleavage site has been reported. For instance, T. Isaksen et. al. (vide supra) reported the oxidation of the C4 position, the non-reducing end moiety, resulting in a keto-sugar at the C4 position, which is in equilibrium with a C4 geminal diol in water solution. The present inventors pose that hydrolysed oxidation products. like for example gluconic acid, are a measure for the performance of the applied LPMO in lignocellulose hydrolysis.

Surprisingly, the present inventors have found that optimal lignocellulose hydrolysis (more than 70% glucan conversion) goes hand in hand with an optimal formation of oxidation products mentioned above like for instance gluconic acid. It will be evident that optimal lignocellulose hydrolysis can only be achieved when (crystalline) cellulose and cello-oligosaccharides are hydrolysed optimally. This optimal hydrolysis by the action of a LPMO will result in the formation of oxidation product, like gluconic acid. No oxidation product means a less efficient hydrolysis of (crystalline) glucan. However, too high levels of oxidation products like gluconic acid will be at the expense of glucose and therefore the glucose yield on (starting) glucan will go down. The amount of formed hydrolysed oxidation products by the oxidation of LPMO of cellulose and/or cello-oligosaccharides is advantageously kept between 3 to 110 g/kg glucan present in the lignocellulosic material by adding a suitable amount of oxygen after the pretreatment and before and/or during the enzymatic hydrolysis to the lignocellulosic material. Preferably, the oxidation product is an aldonic acid and/or geminal diol, more preferably the hydrolysed oxidation product is gluconic acid. Preferably, the amount of formed hydrolysed oxidation products by the oxidation of cellulose and/or cello-oligosaccharides is kept between 4 to 80 g/kg glucan present in the lignocellulosic material, more preferably between 5 to 60 g/kg glucan present in the lignocellulosic material, even more preferably between 6 to 40 g/kg glucan present in the lignocellulosic material, still more preferably between 7 to 30 g/kg glucan present in the lignocellulosic material and most preferably between 8 to 25 g/kg glucan present in the lignocellulosic material. In another embodiment the amount of formed gluconic acid by the oxidation of cellulose and/or cello-oligosaccharides is kept between 3 to 110 g/kg glucan present in the lignocellulosic material, preferably between 3 to 80 g/kg glucan present in the lignocellulosic material, preferably between 3 to 75 g/kg glucan present in the lignocellulosic material, preferably between 3 to 70 g/kg glucan present in the lignocellulosic material, preferably between 3 to 65 g/kg glucan present in the lignocellulosic material, preferably between 3 to 60 g/kg glucan present in the lignocellulosic material, preferably between 3 to 50 g/kg glucan present in the lignocellulosic material, preferably 4 to 50 g/kg glucan present in the lignocellulosic material, more preferably 4 to 30 g/kg glucan present in the lignocellulosic material, even more preferably 4 to 20 g/kg glucan present in the lignocellulosic material and most preferably 5 to 10 g/kg glucan present in the lignocellulosic material.

By the process according to the present invention advantageously higher yields of glucose are obtained. Addition of higher amounts of oxygen will result in more gluconic acid produced instead of glucose and on the other hand in case of lower amounts of oxygen the LPMO is not able to function optimally. Moreover, it was noticed that too high amounts of oxidation products like gluconic acid may inhibit cellulases or hemicellulases or in case the hydrolysate is subsequently fermented, the gluconic acid may have a negative effect on the fermentation by inhibiting the microorganism, such as a yeast, used in the fermentation. The above amounts are the amounts at the end of hydrolysis In general, the amount of oxygen added after the pretreatment and before and/or during the enzymatic hydrolysis to the lignocellulosic material can be controlled or varied in several ways. Restriction of the oxygen supplied is possible by adding only oxygen during part of the hydrolysis time. Another option is adding oxygen at a low concentration, for example by using an mixture of air and recycled air (air leaving the hydrolysis reactor) or by "diluting" air with an inert gas. Increasing the amount of oxygen added, can be obtained by addition of oxygen during longer periods of hydrolysis time, by adding the oxygen at a higher concentration or by adding more air. Another option for changing the oxygen uptake is varying the hydrolysis temperature, a higher temperature will cause a lower maximal saturation concentration of the oxygen in the reactor content. Another way to manage the oxygen concentration is to add an oxygen consumer or an oxygen generator. In case the enzyme may be damaged by the presence or addition of oxygen, milder oxygen supply may be used. In that case, a balance can be found between the improved glucose production and the enzyme performance. The addition of the oxygen to the cellulolytic material can be done before and/or during the enzymatic hydrolysis. In case oxygen is added in gaseous form, oxygen-containing gas can be introduced, for example blown, into the liquid hydrolysis reactor contents of cellulolytic material. In another embodiment of invention the oxygen-containing gas is introduced into the liquid cellulolytic material stream that will enter the hydrolysis reactor. In still another embodiment of the invention the oxygen containing gas is introduced together with the cellulolytic material that enters the hydrolysis reactor or with part of the liquid reactor contents that passes an external loop of the reactor. In most cases the addition of oxygen before entering the hydrolysis reactor is not sufficient enough and oxygen addition may be done during the hydrolysis as well. In another embodiment of the invention the gaseous phase present in the upper part of the reactor (head space) is continuously or discontinuously refreshed with the oxygen-containing gas. In the latter case (vigorous) mixing or stirring is needed to get the oxygen as bubbles and/or by diffusion into the liquid reactor contents preferably in combination with overpressure in the reactor. In general flushing the headspace with air in combination with (vigorous) mixing or stirring may introduce sufficient oxygen into the cellulosic material in the hydrolysis reactor for reactors up to a size of 100 liter to 1 $m^3$. At larger scale, for example in a reactor of 50 $m^3$ or more, for example 100 $m^3$, so much energy is needed for vigorous stirring that from an economic point of view this will not be applied in a commercially operating process.

As described herein, the amount of formed gluconic acid at the end of the enzymatic hydrolysis by the oxidation by LPMO of the lignocellulosic material containing cellulose and/or cello-oligosaccharides is kept between 3 to 80 g/kg glucan present in the lignocellulosic material by adding a suitable amount of oxygen after the pretreatment and before and/or during the enzymatic hydrolysis to the lignocellulosic material. In an embodiment "a suitable amount of oxygen" is 20-10,000 mmol oxygen per kg glucan, preferably 30-5,000 mmol oxygen per kg glucan, more preferably 40-4,000 mmol oxygen per kg glucan and most preferably 50-3,500 mmol oxygen per kg glucan. The amount of oxygen is the entire amount oxygen added during the enzymatic hydrolysis.

According to the present invention the oxygen may be added before the hydrolysis step, during part of the hydrolysis step, during the whole hydrolysis step or a combination of before or during the hydrolysis step. Advantageously, the oxygen is added during the first half of the hydrolysis step. The addition of oxygen during only part of the hydrolysis may be done for example in case oxidation damage of the enzyme(s) occurs. In case the oxygen present in the hydrolysis reactor contents or the sugar product or the hydrolysate formed in the hydrolysis step might influence or disturb the subsequent fermentation step, oxygen addition may be done except for the last part of the hydrolysis and thus (most of) the oxygen is consumed before the hydrolysed biomass enters the fermentation reactor.

Several examples of aeration during the enzymatic hydrolysis process are given in the Examples to show the beneficial effect of the present invention. This beneficial effect is found for several substrates or feedstocks and therefore believed to be present for the hydrolysis of all kind of substrates or feedstocks.

Several examples of enzyme compositions for the enzymatic hydrolysis process are given in the Examples to show the beneficial effect of the present invention. This beneficial effect is found for several enzyme compositions and therefore believed to be present for all kind of hydrolysing enzyme compositions.

To a further preferred embodiment of the invention the oxygen concentration in the liquid phase (DO), wherein the lignocellulosic material is present during the enzymatic hydrolysis, is at least 0.001 mol/$m^3$, preferably at least 0.002 mol/$m^3$, more preferably at least 0.003 mol/$m^3$ and even more preferably more than 0.01 mol/$m^3$, for example more than 0.02 mol/$m^3$ or 0.03 mol/$m^3$. In reactors of less than 1 $m^3$ DO values of below 0.01 mol/$m^3$ or 0.02 mol/$m^3$ will be obtained by slow stirring. Vigorous mixing or stirring at such scale introduces part of the gas phase of the headspace into the reaction liquid. For example, the mixing or stirring may create a whirlpool that draws oxygen into the liquid. In general, flushing the headspace with air in combination with (vigorous) mixing or stirring will introduce sufficient oxygen into the cellulosic material in the hydrolysis reactor for reactors up to a size of 100 liter to 1 $m^3$. At larger scale, for example in a reactor of 50 $m^3$ or more, for example 100 $m^3$, so much energy is needed for vigorous stirring that from economic point of view this will not be applied in a commercially operating process. In general, in large reactors stirring or mixing without introducing air or oxygen will result in DO values of less than 0.01 mol/$m^3$.

To still another preferred embodiment of the invention during the oxygen generation or production the oxygen concentration in the liquid phase (aeration or addition of oxygen), the oxygen concentration in the liquid phase wherein the lignocellulosic material is present during the enzymatic hydrolysis, is preferably at most 80% of the saturation concentration of oxygen under the hydrolysis reaction conditions, more preferably at most 0.12 mol/$m^3$, still more preferably at most 0.09 mol/$m^3$, even more preferably at most 0.06 mol/$m^3$, even still more preferably at most 0.045 mol/$m^3$ and most preferably at most 0.03 mol/$m^3$. The above accounts for the situation when the oxygen transfer rate of the lignocellulosic material is larger than the oxygen uptake rate (OUR) of the lignocellulosic material. When the oxygen consumption (OUR) is higher than the oxygen transfer rate, the oxygen concentration is 0 mol/$m^3$. Temperature and pressure will influence the DO. The preferred and exemplary mol/$m^3$ values given above relate to normal atmospheric pressure and a temperature of about 62° C. The skilled person in the art will appreciate favourable DO values on the basis of the present teachings.

According to a further preferred embodiment of the invention oxygen is consumed in an amount corresponding to between 20 and 5000 mmol molecular oxygen per kg glucan present in the lignocellulosic material. Preferably, oxygen is consumed in an amount corresponding to between 22 and 4500 mmol molecular oxygen per kg glucan present in the lignocellulosic material, between 24 and 4000 mmol molecular oxygen per kg glucan present in the lignocellulosic material, between 26 and 3500 mmol molecular oxygen per kg glucan present in the lignocellulosic material, between 28 and 3400 mmol molecular oxygen per kg glucan present in the lignocellulosic material. The oxygen is added after the pretreatment and before and/or during the enzymatic hydrolysis of the lignocellulosic material, preferably in an amount corresponding to at least 30 mmol molecular oxygen per kg glucan present in the lignocellulosic material, more preferably in an amount corresponding to at least 40 mmol molecular oxygen per kg glucan present in the lignocellulosic material, and most preferably in an amount corresponding to at least 50 mmol molecular oxygen per kg glucan present in the lignocellulosic material. All oxygen that is added to the system will be transferred to the liquid and used for the hydrolysis. This amount can be controlled by measuring and controlling the amount of air brought into the system.

According to a further preferred embodiment of the invention oxygen is consumed in an amount corresponding to between 0.17 and 41.7 mmol molecular oxygen per kg glucan present in the lignocellulosic material per hour. Preferably, oxygen is consumed in an amount corresponding to between 0.18 and 37.5 mmol molecular oxygen per kg glucan present in the lignocellulosic material per hour, between 0.20 and 33.3 mmol molecular oxygen per kg glucan present in the lignocellulosic material per hour, between 0.22 and 29.2 mmol molecular oxygen per kg glucan present in the lignocellulosic material per hour, between 0.23 and 28.3 mmol molecular oxygen per kg glucan present in the lignocellulosic material per hour. More preferably, oxygen is consumed in an amount corresponding to between 0.36 and 27.8 mmol molecular oxygen per kg glucan present in the lignocellulosic material per hour. All oxygen that is added to the system will be transferred to the liquid and used for the hydrolysis. This amount can be controlled by measuring and controlling the amount of air brought into the system. "Per hour" as used herein means per hour of hydrolysis.

The oxygen addition in the form of air or other oxygen-containing gas according to the invention may also be used to at least partially stir or mix the hydrolysis reactor contents. Other ways of oxygen addition include the in situ oxygen generation. For example, the oxygen is generated by electrolysis, oxygen is produced enzymatically, preferably by the addition of peroxide, or oxygen is produced chemically by for example an oxygen generating system such as $KHSO_5$. For example, oxygen is produced from peroxide by catalase. The peroxide can be added in the form of dissolved peroxide or generated by an enzymatic or chemical reaction. In case catalase is used as enzyme to produce oxygen, catalase present in the enzyme composition for the hydrolysis can be used or catalase can be added for this purpose.

The present process of the invention shows advantages especially on pilot plant and industrial scale. According to an embodiment of the invention the reactor for the enzymatic hydrolysis has a volume of 1 m³ or more. Preferably, the reactor has a volume of at least 1 m³, at least 2 m³, at least 3 m³, at least 4 m³, at least 5 m³, at least 6 m³, at least 7 m³, at least 8 m³, at least 9 m³, at least 10 m³, at least 15 m³, at least 20 m³, at least 25 m³, at least 30 m³, at least 35 m³, at least 40 m³, at least 45 m³, at least 50 m³, at least 60 m³, at least 70 m³, at least 75 m³, at least 80 m³, at least 90 m³, at least 100 m³, at least 200 m³, at least 300 m³, at least 400 m³, at least 500 m³, at least 600 m³, at least 700 m³, at least 800 m³, at least 900 m³, at least 1000 m³, at least 1500 m³, at least 2000 m³, at least 2500 m³. In general, the reactor will be smaller than 3000 m³ or 5000 m³. Several reactors may be used. The reactors used in the processes of the present invention may have the same volume, but also may have a different volume.

The inventor poses the theory that especially at large scale insufficient oxygen is available for the hydrolysis which might be due to oxygen transfer limitations in the reactor, for example in the cellulolytic biomass. On lab-scale experiments this oxygen insufficiency may play a less important role. The surface area (or oxygen contact area of the reactor content) to reactor volume ratio is more favourable for small scale experiments than in large scale experiments. Moreover, mixing in small scale experiments is relatively easier than at large scale. During those small scale experiments also the transport of oxygen from the headspace of the hydrolysis reactor is faster than compared to the situation in large scale experiments. This theory is only given as possible explanation of the effect noticed by the inventors and the present invention does not fall or stands with the correctness of this theory. According to a further embodiment of the invention the addition of oxygen may be used to control at least partially the hydrolysis process.

The process of the invention is advantageously applied in combination with the use of thermostable enzymes.

A "thermostable" enzyme means that the enzyme has a temperature optimum 60° C. or higher, for example 70° C. or higher, such as 75° C. or higher, for example 80° C. or higher such as 85° C. or higher. They may for example be isolated from thermophilic microorganisms, or may be designed by the skilled person and artificially synthesized. In one embodiment the polynucleotides may be isolated or obtained from thermophilic or thermotolerant filamentous fungi or isolated from non-thermophilic or non-thermotolerant fungi, but are found to be thermostable.

By "thermophilic fungus" is meant a fungus that grows at a temperature of 50° C. or above. By "themotolerant" fungus is meant a fungus that grows at a temperature of 45° C. or above, having a maximum near 50° C.

Examples of thermophilic fungal strains are *Rasamsonia emersonii* (formerly known as *Talaromyces emersoni*). *Talaromyces emersonii*, *Penicillium geosmithia emersonii* and *Rasamsonia emersonii* are used interchangeably herein.

Suitable thermophilic or thermotolerant fungal cells may be a *Humicola*, *Rhizomucor*, *Myceliophthora*, *Rasamsonia*, *Talaromyces*, *Thermomyces*, *Thermoascus* or *Thielavia* cell, preferably a *Rasamsonia emersonii* cell. Preferred thermophilic or thermotolerant fungi are *Humicola grisea* var. *thermoidea*, *Humicola lanuginosa*, *Myceliophthora thermophila*, *Papulaspora thermophilia*, *Rasamsonia byssochlamydoides*, *Rasamsonia emersonii*, *Rasamsonia argillacea*, *Rasamsonia eburnean*, *Rasamsonia brevistipitata*, *Rasamsonia cylindrospora*, *Rhizomucor pusillus*, *Rhizomucor miehei*, *Talaromyces bacillisporus*, *Talaromyces leycettanus*, *Talaromyces thermophilus*, *Thermomyces lenuginosus*, *Thermoascus crustaceus*, *Thermoascus thermophilus Thermoascus aurantiacus* and *Thielavia terrestris*.

Thermophilic fungi are not restricted to a specific taxonomic order and occur all over the fungal tree of life. Examples are *Rhizomucor* in the Mucorales, *Myceliophthora* in Sordariales and *Talaromyces*, *Thermomyces* and *Thermoascus* in the Eurotiales (Mouchacca 1997). The majority of *Talaromyces* species are mesophiles, but exceptions are species within sections *Emersonii* and *Thermophila*. Section *Emersonii* includes *Talaromyces emersonii*, *Talaromyces byssochlamydoides*, *Talaromyces bacillisporus* and *Talaromyces leycettanus*, all of which grow well at 40° C. *Talaromyces bacillisporus* is thermotolerant, *Talaromyces leycettanus* is thermotolerant to thermophilic, and *Talaromyces emersonii* and *Talaromyces byssochlamydoides* are truly thermophilic (Stolk and Samson, 1972). The sole member of *Talaromyces* section *Thermophila*, *T. thermophi*-

*lus*, grows rapidly at 50° C. (Evans and Stolk, 1971; Evans, 1971; Stolk and Samson, 1972). The current classification of these thermophilic *Talaromyces* species is mainly based on phenotypic and physiological characters, such as their ability to grow above 40° C., ascospore color, the structure of ascornatal covering and the formation of a certain type of anamorph. Stolk and Samson (1972) stated that the members of the section *Emersonii* have anamorphs of either *Paecilomyces* (*T. byssochlamydoides* and *T. leycettanus*) or *Penicillium cylindrosporum* series (*T. emersonii* and *T. bacillisporus*). Later, Pitt (1979) transferred the species belonging to the *Penicillium cylindrosporum* series to the genus *Geosmithia*, based on various characters such as the formation of conidia from terminal pores instead of on collula (necks), a character of *Penicillium* and *Paecilomyces*. Within the genus *Geosmithia*, only *G. argillacea* is thermotolerant, and Stolk et al. (1969) and Evans (1971) proposed a connection with members of *Talaromyces* sect. *Emersonii*. The phylogenetic relationship of the themophilic *Talaromyces* species within *Talaromyces* and the Trichocomaceae is unknown (see J. Houbraken, Antonie van Leeuwenhoek, 2012 February; 101(2):403-21).

*Rasamsonia* is a new genus comprising thermotolerant and thermophilic *Talaromyces* and *Geosmithia* species (J. Houbraken et al., vida supra). Based on phenotypic, physiological and molecular data, Houbraken et al. proposed to transfer the species *T. emersonii, T. byssochlamydoides, T. eburneus, G. argillacea* and *G. cylindrospora* to *Rasamsonia* gen. nov. *Talaromyces emersonii, Penicillium geosmithia emersonii* and *Rasamsonia emersonii* are used interchangeably herein.

Preferred thermophilic fungi are *Rasamsonia byssochlamydoides, Rasamsonia emersonii, Thermomyces lenuginosus, Talaromyces thermophilus, Thermoascus crustaceus, Thermoascus thermophilus* and *Thermoascus aurantiacus*.

"Filamentous fungi" include all filamentous forms of the subdivision *Eumycota* and *Oomycota* (as defined by Hawksworth et al., In Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Agaricus, Aspergillus, Aureobasidium, Beauvaria, Cephalosporium, Ceriporiopsis, Chaetomium paecilomyces, Chrysosporium, Claviceps, Cochiobolus, Coprinus, Cryptococcus, Cyathus, Emericella, Endothia, Endothia mucor, Filibasidium, Fusarium, Geosmithia, Gilocladium, Humicola, Magnaporthe, Mucor, Myceliophthora, Myrothecium, Neocallimastix, Neurospora, Paecilomyces, Penicillium, Piromyces, Panerochaete, Pleurotus, Podospora, Pyricularia, Rasamsonia, Rhizomucor, Rhizopus, Scylatidium, Schizophyllum, Stagonospora, Talaromyces, Thermoascus, Thermomyces, Thielavia, Tolypocladium, Trametes pleurotus, Trichoderma* and *Trichophyton*.

Several strains of filamentous fungi are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL). Examples of such strains include *Aspergillus niger* CBS 513.88, *Aspergillus oryzae* ATCC 20423, IFO 4177, ATCC 1011, ATCC 9576, ATCC14488-14491, ATCC 11601, ATCC12892, *P. chrysogenum* CBS 455.95, *Penicillium citrinum* ATCC 38065, *Penicillium chrysogenum* P2, *Talaromyces emersonii* CBS 393.64, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* C1, Garg 27K, VKM F-3500-D, ATCC44006 and derivatives thereof.

An advantage of expression and production of the enzymes (for example at least two, three or four different cellulases) in a suitable microorganism may be a high enzyme composition yield which can be used in the process of the present invention.

According to the invention, by the addition of oxygen it is possible to attain many process advantages, including optimal temperature conditions, reduced process time, reduced dosage of enzyme, re-use of enzymes and other process optimizations, resulting in reduced costs. Advantageously the invention provides a process in which the hydrolysis step is conducted at improved conditions. The invention also provides a process involving hydrolysis having a reduced process time. Furthermore the invention provides a process, wherein the dosage of enzyme may be reduced and at the same time output of useful hydrolysis product is maintained at the same level. Another advantage of the invention is that the present process involving hydrolysis may result in process conditions which are optimized. A still further advantage of the invention is that the output of useful hydrolysis product of the process involving hydrolysis is increased using the same enzyme dosage.

Stable Enzyme Composition

Stable enzyme composition herein means that the enzyme composition retains activity after 30 hours of hydrolysis reaction time, preferably at least 10%, 20%, 30%, 40%, 50%, 60%, 65%, 70%, 75%, 80% 85%, 90%, 95%, 96%, 97%, 98%, 99% or 100% of its initial activity after 30 hours of hydrolysis reaction time. Preferably, the enzyme composition retains activity after 40, 50, 60, 70, 80, 90 100, 150, 200, 250, 300, 350, 400, 450, 500 hours of hydrolysis reaction time.

In an embodiment the enzyme composition used in the processes of the present invention is derived from a fungus or the enzyme composition used in the processes of the present invention comprises a fungal enzyme. In an embodiment the enzyme composition is derived from a filamentous fungus or the enzyme composition comprises a filamentous fungal enzyme. The processes of the invention are advantageously applied in combination with enzyme compositions derived from a microorganism of the genus *Rasamsonia*, or the enzyme composition comprises a *Rasamsonia* enzyme.

The enzyme composition may be prepared by fermentation of a suitable substrate with a suitable microorganism, e.g. *Rasamsonia emersonii* or *Aspergillus niger* wherein the enzyme composition is produced by the microorganism. The microorganism may be altered to improve or to make the cellulase composition. For example, the microorganism may be mutated by classical strain improvement procedures or by recombinant DNA techniques. Therefore the microorganisms mentioned herein can be used as such to produce the cellulase composition or may be altered to increase the production or to produce an altered cellulase composition which might include heterologous cellulases, thus enzymes that are not originally produced by that microorganism. Preferably, a fungus, more preferably a filamentous fungus, is used to produce the cellulase composition. Advantageously, a thermophilic or thermotolerant microorganism is used. Optionally, a substrate is used that induces the expression of the enzymes in the enzyme composition during the production of the enzyme composition.

The enzyme composition is used to release sugars from lignocellulose that comprises polysaccharides. The major polysaccharides are cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucoronic acid and other hexoses and pentoses occurs under the action of different enzymes acting in concert. By sugar product is meant the enzymatic hydrolysis product of the feedstock or lignocellulosic material. The sugar product will comprise soluble sugars, including both monomers and multimers, preferably will comprise glucose. Examples of other sugars are cellobiose, xylose, arabinose, galactose, fructose, mannose, rhamnose, ribose, galacturonic acid, glucoronic acid and other hexoses and pentoses. The sugar product may be used as such or may be further processed for example purified.

In addition, pectins and other pectic substances such as arabinans may make up considerably proportion of the dry mass of typically cell walls from non-woody plant tissues (about a quarter to half of dry mass may be pectins).

Cellulose is a linear polysaccharide composed of glucose residues linked by β-1,4 bonds. The linear nature of the cellulose fibers, as well as the stoichiometry of the β-linked glucose (relative to α) generates structures more prone to inter strand hydrogen bonding than the highly branched α-linked structures of starch. Thus, cellulose polymers are generally less soluble, and form more tightly bound fibers than the fibers found in starch.

Enzymes that may be included in the stable enzyme composition used in the invention are now described in more detail:

GH61, endoglucanases (EG) and exo-cellobiohydrolases (CBH) catalyze the hydrolysis of insoluble cellulose to products such as cellooligosaccharides (cellobiose as a main product), while beta-glucosidases (BG) convert the oligosaccharides, mainly cellobiose and cellotriose to glucose.

Hemicellulose is a complex polymer and its composition often varies widely from organism to organism and from one tissue type to another. In general, a main component of hemicellulose is β-1,4-linked xylose, a five carbon sugar. However, this xylose is often branched at 0 to 3 and/or 0 to 2 atom of xylose, and can be substituted with linkages to arabinose, galactose, mannose, glucuronic acid, galacturonic acid or by esterification to acetic acid (and esterification of ferulic acid to arabinose). Hemicellulose can also contain glucan, which is a general term for β-linked six carbon sugars (such as the β-(1,3)(1,4) glucans and heteroglucans mentioned previously) and additionally glucomannans (in which both glucose and mannose are present in the linear backbone, linked to each other by β-linkages).

Xylanases together with other accessory enzymes, for example α-L-arabinofuranosidases, feruloyl and acetylxylan esterases, glucuronidases, and β-xylosidases) catalyze the hydrolysis of hemicelluloses.

Pectic substances include pectins, arabinans, galactans and arabinogalactans. Pectins are the most complex polysaccharides in the plant cell wall. They are built up around a core chain of α(1,4)-linked D-galacturonic acid units interspersed to some degree with L-rhamnose. In any one cell wall there are a number of structural units that fit this description and it has generally been considered that in a single pectic molecule, the core chains of different structural units are continuous with one another.

The principal types of structural unit are: galacturonan (homogalacturonan) which may be substituted with methanol on the carboxyl group and acetate on O-2 and O-3; rhamnogalacturonan I (RGI), in which galacturonic acid units alternate with rhamnose units carrying (1,4)-linked galactan and (1,5)-linked arabinan side-chains. The arabinan side-chains may be attached directly to rhamnose or indirectly through the galactan chains; xylogalacturonan, with single xylosyl units on O-3 of galacturonic acid (closely associated with RGI); and rhamnogalacturonan II (RGII), a particularly complex minor unit containing unusual sugars, for example apiose. An RGII unit may contain two apiosyl residues which, under suitable ionic conditions, can reversibly form esters with borate.

A composition for use in a method of the invention comprises preferably at least two activities, although typically a composition will comprise more than two activities, for example, three, four, five, six, seven, eight, nine or more. Typically, a composition of the invention may comprise at least two different celulases or two cellulases and at least one hemicellulase. A composition of the invention may comprise cellulases, but no xylanases. In addition, a composition of the invention may comprise auxiliary enzyme activity, i.e. additional activity which, either directly or indirectly leads to lignocellulose degradation. Examples of such auxiliary activities are mentioned herein.

Thus, a composition for use in the invention may comprise GH61, endoglucanase activity and/or cellobiohydrolase activity and/or beta-glucosidase activity. A composition for use in the invention may comprise more than one enzyme activity in one or more of those classes. For example, a composition for use in the invention may comprise two endoglucanase activities, for example, endo-1,3(1,4)-β glucanase activity and endo-β-1,4-glucanase activity. Such a composition may also comprise one or more xylanase activities. Such a composition may comprise an auxiliary enzyme activity.

A composition for use in the current invention may be derived from a fungus, such as a filamentous fungus such as *Rasamsonia*, such as *Rasamsonia emersonii*. In an embodiment a core set of (lignocellulose degrading) enzyme activities may be derived from *Rasamsonia emersonii*. *Rasamsonia emersonii* can provide a highly effective set of activities as demonstrated herein for the hydrolysis of lignocellulosic material. If needed, the set of activities can be supplemented with additional enzyme activities from other sources. Such additional activities may be derived from classical sources and/or produced by a genetically modified organisms.

The activities in a composition for use in the invention may be thermostable. Herein, this means that the activity has a temperature optimum of about 60° C. or higher, for example about 70° C. or higher, such as about 75° C. or higher, for example about 80° C. or higher such as 85° C. or higher. Activities in a composition for use in the invention will typically not have the same temperature optima, but preferably will, nevertheless, be thermostable.

In addition, enzyme activities in a composition for use in the invention may be able to work at low pH. For the purposes of this invention, low pH indicates a pH of about 5.5 or lower, about 5 or lower, about 4.9 or lower, about 4.8 or lower, about 4.7 or lower, about 4.6 or lower, about 4.5 or lower, about 4.4 or lower, about 4.3 or lower, about 4.2 or lower, about 4.1 or lower, about 4.0 or lower about 3.9 or lower, or about 3.8 or lower, about 3.7 or lower, about 3.6 or lower, or about 3.5 or lower.

Activities in a composition for use in the invention may be defined by a combination of any of the above temperature optima and pH values.

The composition used in a method of the invention may comprise, in addition to the activities derived from *Rasamsonia*, a cellulase (for example one derived from a source other than *Rasamsonia*) and/or a hemicellulase (for example one derived from a source other than *Rasamsonia*) and/or a pectinase.

The enzyme composition for use in the processes of the current invention may comprise a cellulase and/or a hemicellulase and/or a pectinase from a source other than *Rasamsonia*. They may be used together with one or more *Rasamsonia* enzymes or they may be used without additional *Rasamsonia* enzymes being present.

For example, enzymes for use in the processes of the current invention may comprise a beta-glucosidase (BG) from *Aspergillus*, such as *Aspergillus oryzae*, such as the one disclosed in WO 02/095014 or the fusion protein having beta-glucosidase activity disclosed in WO 2008/057637, or *Aspergillus fumigatus*, such as the one disclosed as SEQ ID NO:2 in WO 2005/047499 or SEQ ID NO:5 in WO 2014/130812 or an *Aspergillus fumigatus* beta-glucosidase variant, such as one disclosed in WO 2012/044915, such as one with the following substitutions: F100D, S283G, N456E, F512Y (using SEQ ID NO: 5 in WO 2014/130812 for numbering), or *Aspergillus aculeatus, Aspergillus niger* or *Aspergillus kawachi*. In another embodiment the beta-glucosidase is derived from *Penicillium*, such as *Penicillium brasilianum* disclosed as SEQ ID NO:2 in WO 2007/019442, or from *Trichoderma*, such as *Trichoderma reesei*, such as ones described in U.S. Pat. Nos. 6,022,725, 6,982,159, 7,045,332, 7,005,289, US 2006/0258554 US 2004/0102619. In an embodiment even a bacterial beta-glucosidase can be used. In another embodiment the beta-glucosidase is derived from *Thielavia terrestris* (WO 2011/035029) or *Trichophaea saccata* (WO 2007/019442).

For example, enzymes for use in the processes of the current invention may comprise an endoglucanase (EG) from *Trichoderma*, such as *Trichoderma reesei*; from *Humicola*, such as a strain of *Humicola insolens*; from *Aspergillus*, such as *Aspergillus aculeatus* or *Aspergillus kawachii*; from *Erwinia*, such as *Erwinia carotovara*; from *Fusarium*, such as *Fusarium oxysporum*; from *Thielavia*, such as *Thielavia terrestris*; from *Humicola*, such as *Humicola grisea* var. *thermoidea* or *Humicola insolens*; from *Melanocarpus*, such as *Melanocarpus albomyces*; from *Neurospora*, such as *Neurospora crassa*; from *Myceliophthora*, such as *Myceliophthora thermophila*; from *Cladorrhinum*, such as *Cladorrhinum foecundissimum* and/or from *Chrysosporium*, such as a strain of *Chrysosporium lucknowense*. In an embodiment even a bacterial endoglucanase can be used including, but not limited to, *Acidothermus cellulolyticus* endoglucanase (see WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (see WO 05/093050); and *Thermobifida fusca* endoglucanase V (see WO 05/093050).

For example, enzymes for use in the processes of the current invention may comprise a cellobiohydrolase I from *Aspergillus*, such as *Aspergillus fumigatus*, such as the Cel7A CBH I disclosed in SEQ ID NO:6 in WO 2011/057140 or SEQ ID NO:6 in WO 2014/130812, or from *Trichoderma*, such as *Trichoderma reesei*.

For example, enzymes for use in the processes of the current invention may comprise a cellobiohydrolase II from *Aspergillus*, such as *Aspergillus fumigatus*, such as the one in SEQ ID NO:7 in WO 2014/130812 or from *Trichoderma*, such as *Trichoderma reesei*, or from *Thielavia*, such as *Thielavia terrestris*, such as cellobiohydrolase II CEL6A from *Thielavia terrestris*.

For example, enzymes for use in the processes of the current invention may comprise a GH61 polypeptide (a lytic polysaccharide monooxygenase) from *Thermoascus*, such as *Thermoascus aurantiacus*, such as the one described in WO 2005/074656 as SEQ ID NO:2 and SEQ ID NO:1 in WO2014/130812 and in WO 2010/065830; or from *Thielavia*, such as *Thielavia terrestris*, such as the one described in WO 2005/074647 as SEQ ID NO: 8 or SEQ ID NO:4 in WO2014/130812 and in WO 2008/148131, and WO 2011/035027; or from *Aspergillus*, such as *Aspergillus fumigatus*, such as the one described in WO 2010/138754 as SEQ ID NO:2 or SEQ ID NO: 3 in WO2014/130812; or from *Penicillium*, such as *Penicillium emersonii*, such as the one disclosed as SEQ ID NO:2 in WO 2011/041397 or SEQ ID NO:2 in WO2014/130812. Other suitable GH61 polypeptides include, but are not limited to, *Trichoderma reesei* (see WO 2007/089290), *Myceliophthora thermophila* (see WO 2009/085935, WO 2009/085859, WO 2009/085864, WO 2009/085868), *Penicillium pinophilum* (see WO 2011/005867), *Thermoascus* sp. (see WO 2011/039319), and *Thermoascus crustaceous* (see WO 2011/041504). In one aspect, the GH61 polypeptide is used in the presence of a soluble activating divalent metal cation according to WO 2008/151043, e.g. manganese sulfate. In one aspect, the GH61 polypeptide is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover.

Other cellulolytic enzymes that may be used in the processes of the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648,263, and 5,686,593, to name just a few.

In addition, examples of xylanases useful in the processes of the present invention include, but are not limited to, xylanases from *Aspergillus aculeatus* (see WO 94/21785) *Aspergillus fumigatus* (see WO 2006/078256), *Penicillium pinophilum* (see WO 2011/041405), *Penicillium* sp. (see WO 2010/126772), *Thielavia terrestris* NRRL 8126 (see WO 2009/079210), and *Trichophaea saccata* GH10 (see WO 2011/057083). Examples of beta-xylosidases useful in the processes of the present invention include, but are not limited to, beta-xylosidases from *Neurospora crassa* and *Trichoderma reesei*. Examples of acetylxylan esterases useful in the processes of the present invention include, but are not limited to, acetylxylan esterases from *Aspergillus aculeatus* (see WO 2010/108918), *Chaetomium globosum, Chaetomium gracile, Humicola insolens* DSM 1800 (see WO 2009/073709), *Hypocrea jecorina* (see WO 2005/001036), *Myceliophtera thermophila* (see WO 2010/014880), *Neurospora crassa, Phaeosphaeria nodorum* and *Thielavia terrestris* NRRL 8126 (see WO 2009/042846). Examples of feruloyl esterases (ferulic acid esterases) useful in the processes of the present invention include, but are not limited to, feruloyl esterases form *Humicola insolens* DSM 1800 (see WO 2009/076122), *Neosartorya fischeri, Neurospora crassa, Penicillium aurantiogriseum* (see WO 2009/127729), and *Thielavia terrestris* (see WO 2010/053838 and WO 2010/065448). Examples of arabinofuranosidases useful in the processes of the present invention include, but are not limited to, arabinofuranosidases from *Aspergillus niger, Humicola insolens* DSM 1800 (see WO 2006/114094 and WO 2009/073383) and *M. giganteus* (see WO 2006/114094). Examples of alpha-glucuronidases useful in the processes of the present invention include, but are not limited to, alpha-glucuronidases from *Aspergillus clavatus, Aspergillus fumigatus, Aspergillus niger, Aspergillus terreus, Humicola insolens* (see WO 2010/014706), *Penicillium aurantiogriseum* (see WO 2009/068565) and *Trichoderma reesei.*

A composition for use in the invention may comprise one, two, three, four classes or more of cellulase, for example one, two three or four or all of a GH61, an endoglucanase (EG), one or two exo-cellobiohydrolase (CBH) and a beta-glucosidase (BG). A composition for use in the invention may comprise two or more of any of these classes of cellulase.

A composition of the invention may comprise an activity which has a different type of cellulase activity and/or hemicellulase activity and/or pectinase activity than that provided by the composition for use in a method of the invention. For example, a composition of the invention may comprise one type of cellulase and/or hemicellulase activity and/or pectinase activity provided by a composition as described herein and a second type of cellulase and/or hemicellulase activity and/or pectinase activity provided by an additional cellulose/hemicellulase/pectinase.

Herein, a cellulase is any polypeptide which is capable of degrading or modifying cellulose. A polypeptide which is capable of degrading cellulose is one which is capable of catalysing the process of breaking down cellulose into smaller units, either partially, for example into cellodextrins, or completely into glucose monomers. A cellulase according to the invention may give rise to a mixed population of cellodextrins and glucose monomers when contacted with the cellulase. Such degradation will typically take place by way of a hydrolysis reaction.

LPMO's (lytic polysaccharide monooxygenases) are recently classified by CAZy in family AA9 (Auxiliary Activity Family 9) or family AA10 (Auxiliary Activity Family 10). As mentioned above LPMO is able to open a crystalline glucan structure. LPMO may also affect cello-oligosaccharides. PMO and LPMO are used herein interchangeably. GH61 (glycoside hydrolase family 61 or sometimes referred to EGIV) proteins are (lytic) oxygen-dependent polysaccharide monooxygenases (PMO's/LPMO's) according to the latest literature (Isaksen et al., Journal of Biological Chemistry, vol. 289, no. 5, pp. 2632-2642). Often in literature, these proteins are mentioned to enhance the action of cellulases on lignocellulose substrates. GH61 was originally classified as endoglucanase based on measurement of very weak endo-1,4-β-d-glucanase activity in one family member. The term "GH61" as used herein, is to be understood as a family of enzymes, which share common conserved sequence portions and foldings to be classified in family 61 of the well-established CAZy GH classification system (see, e.g., cazy.org/GH61.html). The glycoside hydrolase family 61 is a member of the family of glycoside hydrolases EC 3.2.1. GH61 are recently now reclassified by CAZy in family AA9 (Auxiliary Activity Family 9). GH61 is used herein as being part of the cellulases. CBM33 (family 33 carbohydrate-binding module) is a LPMO (Isaksen et al., Journal of Biological Chemistry, vol. 289, no. 5, pp. 2632-2642), CAZy has recently reclassified CBM33 in AA10 (Auxiliary Activity Family 10).

Herein, a hemicellulase is any polypeptide which is capable of degrading or modifying hemicellulose. That is to say, a hemicellulase may be capable of degrading or modifying one or more of xylan, glucuronoxylan, arabinoxylan, glucomannan and xyloglucan. A polypeptide which is capable of degrading a hemicellulose is one which is capable of catalysing the process of breaking down the hemicellulose into smaller polysaccharides, either partially, for example into oligosaccharides, or completely into sugar monomers, for example hexose or pentose sugar monomers. A hemicellulase according to the invention may give rise to a mixed population of oligosaccharides and sugar monomers when contacted with the hemicellulase. Such degradation will typically take place by way of a hydrolysis reaction.

Herein, a pectinase is any polypeptide which is capable of degrading or modifying pectin. A polypeptide which is capable of degrading pectin is one which is capable of catalysing the process of breaking down pectin into smaller units, either partially, for example into oligosaccharides, or completely into sugar monomers. A pectinase according to the invention may give rise to a mixed population of oligosacchardies and sugar monomers when contacted with the pectinase. Such degradation will typically take place by way of a hydrolysis reaction.

Accordingly, a composition of the invention may comprise any cellulase, for example, a GH61, a cellobiohydrolase, an endo-β-1,4-glucanase, a beta-glucosidase or a β-(1,3)(1,4)-glucanase.

Herein, a cellobiohydrolase (EC 3.2.1.91) is any polypeptide which is capable of catalysing the hydrolysis of 1,4-β-D-glucosidic linkages in cellulose or cellotetraose, releasing cellobiose from the ends of the chains. This enzyme may also be referred to as cellulase 1,4-β-cellobiosidase, 1,4-β-cellobiohydrolase, 1,4-β-D-glucan cellobiohydrolase, avicelase, exo-1,4-β-D-glucanase, exocellobiohydrolase or exoglucanase.

Herein, an endo-β-1,4-glucanase (EC 3.2.1.4) is any polypeptide which is capable of catalysing the endohydrolysis of 1,4-β-D-glucosidic linkages in cellulose, lichenin or cereal β-D-glucans. Such a polypeptide may also be capable of hydrolyzing 1,4-linkages in β-D-glucans also containing 1,3-linkages. This enzyme may also be referred to as cellulase, avicelase, β-1,4-endoglucan hydrolase, β-1,4-glucanase, carboxymethyl cellulase, celludextrinase, endo-1,4-β-D-glucanase, endo-1,4-β-D-glucanohydrolase, endo-1,4-β-glucanase or endoglucanase.

Herein, a beta-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalase, β-D-glucoside glucohydrolase, cellobiase or gentobiase.

Herein a β-(1,3)(1,4)-glucanase (EC 3.2.1.73) is any polypeptide which is capable of catalyzing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as licheninase, 1,3-1,4-β-D-glucan 4-glucanohydrolase, β-glucanase, endo-β-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3- or 1,4-linkages in beta-D-glucanse when the glucose residue whose reducing group is involved in the linkage to be hydrolysed is itself substituted at C-3. Alternative names include endo-1,3-beta-glucanase, laminarinase, 1,3-(1,3;1,4)-beta-D-glucan 3 (4) glucanohydrolase; substrates include laminarin, lichenin and cereal beta-D-glucans.

A composition of the invention may comprise any hemicellulase, for example, an endoxylanase, a β-xylosidase, a α-L-arabionofuranosidase, an α-D-glucuronidase, an acetyl xylan esterase, a feruloyl esterase, a coumaroyl esterase, an α-galactosidase, a β-galactosidase, a β-mannanase or a β-mannosidase.

Herein, an endoxylanase (EC 3.2.1.8) is any polypeptide which is capable of catalyzing the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyse 1,4 xylosidic linkages in glucuronoarabinoxylans.

Herein, a β-xylosidase (EC 3.2.1.37) is any polypeptide which is capable of catalyzing the hydrolysis of 1,4-β-D-xylans, to remove successive D-xylose residues from the non-reducing termini. Such enzymes may also hydrolyze xylobiose. This enzyme may also be referred to as xylan 1,4-β-xylosidase, 1,4-β-D-xylan xylohydrolase, exo-1,4-β-xylosidase or xylobiase.

Herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

Herein, an α-D-glucuronidase (EC 3.2.1.139) is any polypeptide which is capable of catalyzing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyse 4-O-methylated glucuronic acid, which can also be present as a substituent in xylans. Alternative is EC 3.2.1.131: xylan alpha-1,2-glucuronosidase, which catalyses the hydrolysis of alpha-1,2-(4-O-methyl)glucuronosyl links.

Herein, an acetyl xylan esterase (EC 3.1.1.72) is any polypeptide which is capable of catalyzing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacetylglycerol. Such a polypeptide typically does not act on acetylated mannan or pectin.

Herein, a feruloyl esterase (EC 3.1.1.73) is any polypeptide which is capable of catalyzing a reaction of the form: feruloyl-saccharide+$H_2O$=ferulate+saccharide. The saccharide may be, for example, an oligosaccharide or a polysaccharide. It may typically catalyze the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin.

Herein, a coumaroyl esterase (EC 3.1.1.73) is any polypeptide which is capable of catalyzing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

Herein, an α-galactosidase (EC 3.2.1.22) is any polypeptide which is capable of catalyzing the hydrolysis of of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

Herein, a β-galactosidase (EC 3.2.1.23) is any polypeptide which is capable of catalyzing the hydrolysis of terminal non-reducing β-D-galactose residues in β-D-galactosides. Such a polypeptide may also be capable of hydrolyzing α-L-arabinosides. This enzyme may also be referred to as exo-(1->4)-β-D-galactanase or lactase.

Herein, a β-mannanase (EC 3.2.1.78) is any polypeptide which is capable of catalyzing the random hydrolysis of 1,4-β-D-mannosidic linkages in mannans, galactomannans and glucomannans. This enzyme may also be referred to as mannan endo-1,4-β-mannosidase or endo-1,4-mannanase.

Herein, a β-mannosidase (EC 3.2.1.25) is any polypeptide which is capable of catalyzing the hydrolysis of terminal, non-reducing β-D-mannose residues in β-D-mannosides. This enzyme may also be referred to as mannanase or mannase.

A composition of the invention may comprise any pectinase, for example an endo-polygalacturonase, a pectin methyl esterase, an endo-galactanase, a beta-galactosidase, a pectin acetyl esterase, an endo-pectin lyase, pectate lyase, alpha-rhamnosidase, an exo-galacturonase, an expolygalacturonate lyase, a rhamnogalacturonan hydrolase, a rhamnogalacturonan lyase, a rhamnogalacturonan acetyl esterase, a rhamnogalacturonan galacturonohydrolase, a xylogalacturonase.

Herein, an endo-polygalacturonase (EC 3.2.1.15) is any polypeptide which is capable of catalyzing the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

Herein, a pectin methyl esterase (EC 3.1.1.11) is any enzyme which is capable of catalyzing the reaction: pectin+n $H_2O$=n methanol+pectate. The enzyme may also been known as pectinesterase, pectin demethoxylase, pectin methoxylase, pectin methylesterase, pectase, pectinoesterase or pectin pectylhydrolase.

Herein, an endo-galactanase (EC 3.2.1.89) is any enzyme capable of catalyzing the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

Herein, a pectin acetyl esterase is defined herein as any enzyme which has an acetyl esterase activity which catalyzes the deacetylation of the acetyl groups at the hydroxyl groups of GalUA residues of pectin Herein, an endo-pectin lyase (EC 4.2.2.10) is any enzyme capable of catalyzing the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

Herein, a pectate lyase (EC 4.2.2.2) is any enzyme capable of catalyzing the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

Herein, an alpha-rhamnosidase (EC 3.2.1.40) is any polypeptide which is capable of catalyzing the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

Herein, exo-galacturonase (EC 3.2.1.82) is any polypeptide capable of hydrolysis of pectic acid from the non-reducing end, releasing digalacturonate. The enzyme may also be known as exo-poly-α-galacturonosidase, exopolygalacturonosidase or exopolygalacturanosidase.

Herein, exo-galacturonase (EC 3.2.1.67) is any polypeptide capable of catalyzing: $(1,4-\alpha-D-galacturonide)_n + H_2O = (1,4-\alpha-D-galacturonide)_{n-1} + D$-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

Herein, exopolygalacturonate lyase (EC 4.2.2.9) is any polypeptide capable of catalyzing eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

Herein, rhamnogalacturonan hydrolase is any polypeptide which is capable of hydrolyzing the linkage between galactosyluronic acid acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

Herein, rhamnogalacturonan lyase is any polypeptide which is any polypeptide which is capable of cleaving α-L-Rhap-(1→4)-α-D-GalpA linkages in an endo-fashion in rhamnogalacturonan by beta-elimination.

Herein, rhamnogalacturonan acetyl esterase is any polypeptide which catalyzes the deacetylation of the backbone of alternating rhamnose and galacturonic acid residues in rhamnogalacturonan.

Herein, rhamnogalacturonan galacturonohydrolase is any polypeptide which is capable of hydrolyzing galacturonic acid from the non-reducing end of strictly alternating rhamnogalacturonan structures in an exo-fashion.

Herein, xylogalacturonase is any polypeptide which acts on xylogalacturonan by cleaving the β-xylose substituted galacturonic acid backbone in an endo-manner. This enzyme may also be known as xylogalacturonan hydrolase.

Herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

Herein, endo-arabinanase (EC 3.2.1.99) is any polypeptide which is capable of catalyzing endohydrolysis of 1,5-α-arabinofuranosidic linkages in 1,5-arabinans. The enzyme may also be known as endo-arabinase, arabinan endo-1,5-α-L-arabinosidase, endo-1,5-α-L-arabinanase, endo-α-1,5-arabanase, endo-arabanase or 1,5-α-L-arabinan 1,5-α-L-arabinanohydrolase.

A composition of the invention will typically comprise at least two cellulases and optionally at least one hemicellulase and optionally at least one pectinase (one of which is a polypeptide according to the invention). A composition of the invention may comprise a GH61, a cellobiohydrolase, an endoglucanase and/or a beta-glucosidase. Such a composition may also comprise one or more hemicellulases and/or one or more pectinases.

In addition, one or more (for example two, three, four or all) of an amylase, a protease, a lipase, a ligninase, a hexosyltransferase, a glucuronidase or an expansin or a cellulose induced protein or a cellulose integrating protein or like protein may be present in a composition of the invention (these are referred to as auxiliary activities above).

"Protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the invention incorporated herein by reference. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin.

"Ligninase" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.1.14), manganese peroxidases (EC 1.11.1.13), laccases (EC 1.10.3.2) and feruloyl esterases (EC 3.1.1.73).

"Hexosyltransferase" (2.4.1-) includes enzymes which are capable of catalyzing a transferase reaction, but which can also catalyze a hydrolysis reaction, for example of cellulose and/or cellulose degradation products. An example of a hexosyltransferase which may be used in the invention is a ß-glucanosyltransferase. Such an enzyme may be able to catalyze degradation of (1,3)(1,4)glucan and/or cellulose and/or a cellulose degradation product.

"Glucuronidase" includes enzymes that catalyze the hydrolysis of a glucoronoside, for example β-glucuronoside to yield an alcohol. Many glucuronidases have been characterized and may be suitable for use in the invention, for example β-glucuronidase (EC 3.2.1.31), hyaluronoglucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

A composition for use in the invention may comprise an expansin or expansin-like protein, such as a swollenin (see Salheimo et al., Eur. J. Biohem. 269, 4202-4211, 2002) or a swollenin-like protein.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. For the purposes of this invention, an expansin-like protein or swollenin-like protein may comprise one or both of such domains and/or may disrupt the structure of cell walls (such as disrupting cellulose structure), optionally without producing detectable amounts of reducing sugars.

A composition for use in the invention may comprise a cellulose induced protein, for example the polypeptide product of the cip1 or cip2 gene or similar genes (see Foreman et al., J. Biol. Chem. 278(34), 31988-31997, 2003), a cellulose/cellulosome integrating protein, for example the polypeptide product of the cipA or cipC gene, or a scaffoldin or a scaffoldin-like protein. Scaffoldins and cellulose integrating proteins are multi-functional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM) that mediates attachment of the cellulosome to its substrate. A scaffoldin or cellulose integrating protein for the purposes of this invention may comprise one or both of such domains.

A composition for use in the current invention may also comprise a catalase. The term "catalase" means a hydrogen-peroxide: hydrogen-peroxide oxidoreductase (EC 1.11.1.6 or EC 1.11.1.21) that catalyzes the conversion of two hydrogen peroxides to oxygen and two waters. Catalase activity can be determined by monitoring the degradation of hydrogen peroxide at 240 nm based on the following reaction: $2H_2O_2 \rightarrow 2H_2O+O_2$. The reaction is conducted in 50 mM phosphate pH 7.0 at 25° C. with 10.3 mM substrate ($H_2O_2$) and approximately 100 units of enzyme per ml. Absorbance is monitored spectrophotometrically within 16-24 seconds, which should correspond to an absorbance reduction from 0.45 to 0.4. One catalase activity unit can be expressed as one micromole of $H_2O_2$ degraded per minute at pH 7.0 and 25° C.

A composition for use in a method of the invention may be composed of a member of each of the classes of enzymes mentioned above, several members of one enzyme class, or any combination of these enzymes classes or helper proteins (i.e. those proteins mentioned herein which do not have enzymatic activity per se, but do nevertheless assist in lignocellulosic degradation).

A composition for use in a method of the invention may be composed of enzymes from (1) commercial suppliers; (2) cloned genes expressing enzymes; (3) complex broth (such as that resulting from growth of a microbial strain in media, wherein the strains secrete proteins and enzymes into the media; (4) cell lysates of strains grown as in (3); and/or (5) plant material expressing enzymes. Different enzymes in a composition of the invention may be obtained from different sources.

The enzymes can be produced either exogenously in microorganisms, yeasts, fungi, bacteria or plants, then isolated and added, for example, to lignocellulosic feedstock. Alternatively, the enzymes are produced, but not isolated, and crude cell mass fermentation broth, or plant material (such as corn stover or wheat straw), and the like may be added to, for example, the feedstock. Alternatively, the crude cell mass or enzyme production medium or plant material may be treated to prevent further microbial growth (for example, by heating or addition of antimicrobial agents), then added to, for example, a feedstock. These crude enzyme mixtures may include the organism producing the enzyme. Alternatively, the enzyme may be produced in a fermentation that uses (pre-treated) feedstock (such as corn stover or wheat straw) to provide nutrition to an organism that produces an enzyme(s). In this manner, plants that produce the enzymes may themselves serve as a lignocellulosic feedstock and be added into lignocellulosic feedstock.

In the uses and methods described herein, the components of the compositions described above may be provided concomitantly (i.e. as a single composition per se) or separately or sequentially.

The invention thus relates to methods in which the composition described above are used and to uses of the composition in industrial processes.

In an embodiment of the processes according to the present invention the enzyme composition is in the form of a whole fermentation broth of a fungus. In an embodiment the enzyme compositions may be a whole fermentation broth as described below. The whole fermentation broth can be prepared from fermentation of non-recombinant and/or recombinant filamentous fungi. In an embodiment the filamentous fungus is a recombinant filamentous fungus comprising one or more genes which can be homologous or heterologous to the filamentous fungus. In an embodiment, the filamentous fungus is a recombinant filamentous fungus comprising one or more genes which can be homologous or heterologous to the filamentous fungus wherein the one or more genes encode enzymes that can degrade a cellulosic substrate. The whole fermentation broth may comprise any of the polypeptides or any combination thereof.

Preferably, the enzyme composition is whole fermentation broth wherein the cells are killed. The whole fermentation broth may contain organic acid(s) (used for killing the cells), killed cells and/or cell debris, and culture medium.

Generally, the filamentous fungi is cultivated in a cell culture medium suitable for production of enzymes capable of hydrolyzing a cellulosic substrate. The cultivation takes place in a suitable nutrient medium comprising carbon and nitrogen sources and inorganic salts, using procedures known in the art. Suitable culture media, temperature ranges and other conditions suitable for growth and cellulase and/or hemicellulase and/or pectinase production are known in the art. The whole fermentation broth can be prepared by growing the filamentous fungi to stationary phase and maintaining the filamentous fungi under limiting carbon conditions for a period of time sufficient to express the one or more cellulases and/or hemicellulases and/or pectinases.

Once enzymes, such as cellulases and/or hemicellulases and/or pectinases, are secreted by the filamentous fungi into the fermentation medium, the whole fermentation broth can be used. The whole fermentation broth of the present invention may comprise filamentous fungi. In some embodiments, the whole fermentation broth comprises the unfractionated contents of the fermentation materials derived at the end of the fermentation. Typically, the whole fermentation broth comprises the spent culture medium and cell debris present after the filamentous fungi is grown to saturation, incubated under carbon-limiting conditions to allow protein synthesis (particularly, expression of cellulases and/or hemicellulases and/or pectinases). In some embodiments, the whole fermentation broth comprises the spent cell culture medium, extracellular enzymes and filamentous fungi. In some embodiments, the filamentous fungi present in whole fermentation broth can be lysed, permeabilized, or killed using methods known in the art to produce a cell-killed whole fermentation broth. In an embodiment, the whole fermentation broth is a cell-killed whole fermentation broth, wherein the whole fermentation broth containing the filamentous fungi cells are lysed or killed. In some embodiments, the cells are killed by lysing the filamentous fungi by chemical and/or pH treatment to generate the cell-killed whole broth of a fermentation of the filamentous fungi. In some embodiments, the cells are killed by lysing the filamentous fungi by chemical and/or pH treatment and adjusting the pH of the cell-killed fermentation mix to a suitable pH. In an embodiment, the whole fermentation broth comprises a first organic acid component comprising at least one 1-5 carbon organic acid and/or a salt thereof and a second organic acid component comprising at least 6 or more carbon organic acid and/or a salt thereof. In an embodiment, the first organic acid component is acetic acid, formic acid, propionic acid, a salt thereof, or any combination thereof and the second organic acid component is benzoic acid, cyclohexanecarboxylic acid, 4-methylvaleric acid, phenylacetic acid, a salt thereof, or any combination thereof.

The term "whole fermentation broth" as used herein refers to a preparation produced by cellular fermentation that undergoes no or minimal recovery and/or purification. For example, whole fermentation broths are produced when microbial cultures are grown to saturation, incubated under carbon-limiting conditions to allow protein synthesis (e.g., expression of enzymes by host cells) and secretion into cell culture medium. Typically, the whole fermentation broth is unfractionated and comprises spent cell culture medium, extracellular enzymes, and microbial, preferably non-viable, cells.

If needed, the whole fermentation broth can be fractionated and the one or more of the fractionated contents can be used. For instance, the killed cells and/or cell debris can be removed from a whole fermentation broth to provide a composition that is free of these components.

The whole fermentation broth may further comprise a preservative and/or antimicrobial agent. Such preservatives and/or agents are known in the art.

The whole fermentation broth as described herein is typically a liquid, but may contain insoluble components, such as killed cells, cell debris, culture media components, and/or insoluble enzyme(s). In some embodiments, insoluble components may be removed to provide a clarified whole fermentation broth.

In an embodiment, the whole fermentation broth may be supplemented with one or more enzyme activities that are not expressed endogenously, or expressed at relatively low level by the filamentous fungi, to improve the degradation of the cellulosic substrate, for example, to fermentable sugars such as glucose or xylose. The supplemental enzyme(s) can be added as a supplement to the whole fermentation broth and the enzymes may be a component of a separate whole fermentation broth, or may be purified, or minimally recovered and/or purified.

In an embodiment, the whole fermentation broth comprises a whole fermentation broth of a fermentation of a recombinant filamentous fungi overexpressing one or more enzymes to improve the degradation of the cellulosic substrate. Alternatively, the whole fermentation broth can comprise a mixture of a whole fermentation broth of a fermentation of a non-recombinant filamentous fungus and a recombinant filamentous fungus overexpressing one or more enzymes to improve the degradation of the cellulosic substrate. In an embodiment, the whole fermentation broth comprises a whole fermentation broth of a fermentation of a filamentous fungi overexpressing beta-glucosidase. Alternatively, the whole fermentation broth for use in the present methods and reactive compositions can comprise a mixture of a whole fermentation broth of a fermentation of a non-recombinant filamentous fungus and a whole fermentation broth of a fermentation of a recombinant filamentous fungi overexpressing a beta-glucosidase.

In an embodiment the process for the preparation of a sugar product from lignocellulosic material comprises the following steps (a) optionally, pretreatment of the lignocellulosic material, (b) optionally, washing of the optionally pretreated lignocellulosic material, (c) producing an enzyme composition comprising at least two cellulases and whereby the enzyme composition at least comprises LPMO by culturing a fungus under conditions which allow for expression of the enzyme composition, (d) enzymatic hydrolysis of the optionally washed and/or optionally pretreated lignocellulosic material using the enzyme composition, and (e) optionally, recovery of a glucose-containing composition, wherein the amounts of formed hydrolysed oxidation products at the end of the enzymatic hydrolysis by the oxidation by LPMO of the lignocellulosic material containing cellulose and/or cello-oligosaccharides is kept between 3 to 110 g/kg glucan present in the lignocellulosic material by adding a suitable amount of oxygen after the pretreatment and before and/or during the enzymatic hydrolysis to the lignocellulosic material, preferably the formed hydrolysed oxidation product is gluconic acid, an aldonic acid and/or geminal diol, more preferably the hydrolysed oxidation product is gluconic acid.

In an embodiment the process for the preparation of a fermentation product from lignocellulosic material comprises the following steps (a) optionally, pretreatment of the lignocellulosic material, (b) optionally, washing of the optionally pretreated lignocellulosic material, (c) producing an enzyme composition comprising at least two cellulases and whereby the enzyme composition at least comprises LPMO by culturing a fungus under conditions which allow for expression of the enzyme composition, (d) enzymatic hydrolysis of the optionally washed and/or optionally pretreated lignocellulosic material using the enzyme composition, (e) fermentation of the hydrolysed lignocellulosic material to produce a fermentation product, and (f) optionally, recovery of a fermentation product, wherein the amounts of formed hydrolysed oxidation products at the end of the enzymatic hydrolysis by the oxidation by LPMO of the lignocellulosic material containing cellulose and/or cello-oligosaccharides is kept between 3 to 110 g/kg glucan present in the lignocellulosic material by adding a suitable amount of oxygen after the pre-treatment and before and/or during the enzymatic hydrolysis to the lignocellulosic material, preferably the formed hydrolysed oxidation product is gluconic acid, an aldonic acid and/or geminal diol, more preferably the hydrolysed oxidation product is gluconic acid.

As indicated above, in a preferred embodiment the fungus is a filamentous fungus, preferably the fungus belongs to the genus *Rasamsonia* or *Aspergillus*. In an embodiment the culturing of the fungus is conducted under aerobic conditions. A person skilled in the art is well aware of fermentor designs for aerobic cultivation such as for instance stirred tanks and bubble columns. Generally, the fungi are cultivated in a cell culture medium suitable for production of the enzyme composition of interest. The cultivation takes place in a suitable nutrient medium comprising carbon and nitrogen sources and inorganic salts, using procedures known in the art. Suitable culture media, temperature ranges and other conditions suitable for growth and enzyme production are known in the art. Examples thereof are described herein. The enzyme composition can be prepared by growing the fungi to stationary phase and maintaining the fungi under limiting carbon conditions for a period of time sufficient to express the enzymes. Once the enzymes of interest are secreted by the fungi into the fermentation medium, the enzyme composition can be used. The process step of producing an enzyme composition comprising at least two cellulases and whereby the enzyme composition at least comprises LPMO by culturing a fungus under conditions which allow for expression of the enzyme composition as described herein can be preceded by a process for propagating the fungus. Propagation may comprise several steps in shake flasks, small containers and large containers.

Lignocellulosic Material

Lignocellulosic material herein includes any lignocellulosic and/or hemicellulosic material. Lignocellulosic material suitable for use as feedstock in the invention includes biomass, e.g. virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane, cane straw, sugar cane bagasse, sugar cane trash, switch grass, miscanthus, energy cane, corn, corn stover, corn husks, corn cobs, canola stems, soybean stems, sweet sorghum, corn kernel including fiber from kernels, products and by-products from milling of grains such as corn, wheat and barley (including wet milling and dry milling) often called "bran or fibre" as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the aforementioned singularly or in any combination or mixture thereof.

Cellulose is an organic compound with the formula $(C_6H_{10}O_5)_n$, a polysaccharide consisting of a linear chain of several hundred to over ten thousand β(1→4) linked D-glucose units. A glucan molecule is a polysaccharide of D-glucose monomers linked by glycosidic bonds. Herein glucan and cellulose are used interchangeably for a polysaccharide of D-glucose monomers linked by glycosidic bonds. Methods for the quantitative analysis of glucan or polysaccharide compositions are well-known and described in the art and are for example summarized in Carvalho de Souza et al., Carbohydrate Polymers 95 (2013) 657-663. In general, 50 to 70% of the glucan is crystalline cellulose, the remainder is amorphous cellulose.

Pretreatment

The lignocellulosic material used in the present invention may be washed and/or pretreated. The feedstock may optionally be pretreated with heat, mechanical and/or chemical modification or any combination of such methods in order to enhance the accessibility of the substrate to enzymatic hydrolysis and/or hydrolyse the hemicellulose and/or solubilize the hemicellulose and/or cellulose and/or lignin, in any way known in the art. In one embodiment, the pretreatment is conducted treating the lignocellulose with steam explosion, hot water treatment or treatment with dilute acid or dilute base.

In an embodiment the lignocellulosic material is pretreated before and/or during the enzymatic hydrolysis. Pretreatment methods are known in the art and include, but are not limited to, heat, mechanical, chemical modification, biological modification and any combination thereof. Pretreatment is typically performed in order to enhance the accessibility of the lignocellulosic material to enzymatic hydrolysis and/or hydrolyse the hemicellulose and/or solubilize the hemicellulose and/or cellulose and/or lignin, in the lignocellulosic material. In an embodiment, the pretreatment comprises treating the lignocellulosic material with steam explosion, hot water treatment or treatment with dilute acid or dilute base. Examples of pretreatment methods include, but are not limited to, steam treatment (e.g. treatment at 100-260° C., at a pressure of 7-45 bar, at neutral pH, for 1-10 minutes), dilute acid treatment (e.g. treatment with 0.1-5% $H_2SO_4$ and/or $SO_2$ and/or $HNO_3$ and/or HCl, in presence or absence of steam, at 120-200° C., at a pressure of 2-15 bar, at acidic pH, for 2-30 minutes), organosolv treatment (e.g. treatment with 1-1.5% $H_2SO_4$ in presence of organic solvent and steam, at 160-200° C., at a pressure of 7-30 bar, at acidic pH, for 30-60 minutes), lime treatment (e.g. treatment with 0.1-2% $NaOH/Ca(OH)_2$ in the presence of water/steam at 60-160° C., at a pressure of 1-10 bar, at alkaline pH, for 60-4800 minutes), ARP treatment (e.g. treatment with 5-15% $NH_3$, at 150-180° C., at a pressure of 9-17 bar, at alkaline pH, for 10-90 minutes), AFEX treatment (e.g. treatment with >15% $NH_3$, at 60-140° C., at a pressure of 8-20 bar, at alkaline pH, for 5-30 minutes).

Washing Step

Optionally, the process according to the invention comprises a washing step. The optional washing step may be used to remove water soluble compounds that may act as inhibitors for the fermentation step. The washing step may be conducted in known manner.

The lignocellulosic material may be washed. In an embodiment the lignocellulosic material may be washed after the pretreatment. The washing step may be used to remove water soluble compounds that may act as inhibitors for the fermentation and/or hydrolysis step. The washing step may be conducted in manner known to the skilled person. Next to washing, other detoxification methods do exist. The pretreated lignocellulosic material may also be detoxified by any (or any combination) of these methods which include, but are not limited to, solid/liquid separation, vacuum evaporation, extraction, adsorption, neutralization, overliming, addition of reducing agents, addition of detoxifying enzymes such as laccases or peroxidases, addition of microorganisms capable of detoxification of hydrolysates.

Enzymatic Hydrolysis

The enzyme composition used in the process of the invention can extremely effectively hydrolyze lignocellulolytic material, for example corn stover, wheat straw, cane straw, and/or sugar cane bagasse, which can then be further converted into a useful product, such as ethanol, biogas, butanol, lactic acid, a plastic, an organic acid, a solvent, an animal feed supplement, a pharmaceutical, a vitamin, an amino acid, an enzyme or a chemical feedstock. Additionally, intermediate products from a process following the hydrolysis, for example lactic acid as intermediate in biogas production, can be used as building block for other materials. The present invention is exemplified with the production of ethanol but this is done as exemplification only rather than as limitation, the other mentioned useful products can be produced equally well.

The process according to the invention comprises an enzymatic hydrolysis step. The enzymatic hydrolysis includes, but is not limited to, hydrolysis for the purpose of liquefaction of the feedstock and hydrolysis for the purpose of releasing sugar from the feedstock or both. In this step optionally pretreated and optionally washed lignocellulosic material is brought into contact with the enzyme composition according to the invention. Depending on the lignocellulosic material and the pretreatment, the different reaction conditions, e.g. temperature, enzyme dosage, hydrolysis reaction time and dry matter concentration, may be adapted by the skilled person in order to achieve a desired conversion of lignocellulose to sugar. Some indications are given hereafter.

In an embodiment the enzymatic hydrolysis comprises at least a liquefaction step wherein the lignocellulosic material is hydrolysed in at least a first container, and a saccharification step wherein the liquefied lignocellulosic material is hydrolysed in the at least first container and/or in at least a second container. Saccharification can be done in the same container as the liquefaction (i.e. the at least first container), it can also be done in a separate container (i.e. the at least second container). So, in the enzymatic hydrolysis of the processes according to the present invention liquefaction and saccharification may be combined. Alternatively, the liquefaction and saccharification may be separate steps. Liquefaction and saccharification may be performed at different temperatures, but may also be performed at a single temperature. In an embodiment the temperature of the liquefaction is higher than the temperature of the saccharification. Liquefaction is preferably carried out at a temperature of 60-75° C. and saccharification is preferably carried out at a temperature of 50-65° C.

The enzymes used in the enzymatic hydrolysis may be added before and/or during the enzymatic hydrolysis. In case the enzymatic hydrolysis comprises a liquefaction step and saccharification step, additional enzymes may be added during and/or after the liquefaction step. The additional enzymes may be added before and/or during the saccharification step. Additional enzymes may also be added after the saccharification step.

In one aspect of the invention the hydrolysis is conducted at a temperature of 45° C. or more, 50° C. or more, 55° C. or more, 60° C. or more, 65° C. or more, or 70° C. or more. The high temperature during hydrolysis has many advantages, which include working at the optimum temperature of the enzyme composition, the reduction of risk of (bacterial) contamination, reduced viscosity, smaller amount of cooling water required, use of cooling water with a higher temperature, re-use of the enzymes and more.

The viscosity of the lignocellulosic material in the one or more containers used for the enzymatic hydrolysis is kept between 10 and 4000 cP, between 10 and 2000 cP, preferably between 10 and 1000 cP.

In case the process comprises an enzymatic hydrolysis comprising a liquefaction step and a saccharification step, the viscosity of the lignocellulosic material in the liquefaction step is kept between 10 and 4000 cP, between 10 and 2000 cP, preferably between 10 and 1000 cP and/or the viscosity of the lignocellulosic material in the saccharification step is kept between 10 and 1000 cP, between 10 and 900 cP, preferably between 10 and 800 cP.

The viscosity can be determined with a Brookfield DV III Rheometer at the temperature used for the hydrolysis.

In a further aspect of the invention, the amount of enzyme composition added (herein also called enzyme dosage or enzyme load) is low. In an embodiment the amount of enzyme is 6 mg protein/g dry matter weight or lower, 5 mg protein/g dry matter or lower, 4 mg protein/g dry matter or lower, 3 mg protein/g dry matter or lower, 2 mg protein/g dry matter or lower, or 1 mg protein/g dry matter or lower (expressed as protein in mg protein/g dry matter). In an embodiment, the amount of enzyme is 0.5 mg enzyme/g dry matter weight or lower, 0.4 mg enzyme composition/g dry matter weight or lower, 0.3 mg enzyme/g dry matter weight or lower, 0.25 mg enzyme/g dry matter weight or lower, 0.20 mg enzyme/g dry matter weight or lower, 0.18 mg enzyme/g dry matter weight or lower, 0.15 mg enzyme/g dry matter weight or lower or 0.10 mg enzyme/g dry matter weight or lower (expressed as total of cellulase enzymes in mg enzyme/g dry matter). Low enzyme dosage is possible, since because of the activity and stability of the enzymes, it is possible to increase the hydrolysis reaction time.

In a further aspect of the invention, the hydrolysis reaction time is 5 hours or more, 10 hours or more, 20 hours or more, 40 hours or more, 50 hours or more, 60 hours or more, 70 hours or more, 80 hours or more, 90 hours or more, 100 hours or more, 120 hours or more, 130 h or more. In another aspect, the hydrolysis reaction time is 5 to 150 hours, 40 to 130 hours, 50 to 120 hours, 60 to 120 hours, 60 to 110 hours, 60 to 100 hours, 70 to 100 hours, 70 to 90 hours or 70 to 80 hours. Due to the stability of the enzyme composition longer hydrolysis reaction times are possible with corresponding higher sugar yields.

The pH during hydrolysis may be chosen by the skilled person. In a further aspect of the invention, the pH during the hydrolysis may be 3.0 to 6.4. The stable enzymes of the invention may have a broad pH range of up to 2 pH units, up to 3 pH units, up to 5 pH units. The optimum pH may lie within the limits of pH 2.0 to 8.0, 3.0 to 8.0, 3.5 to 7.0, 3.5 to 6.0, 3.5 to 5.0, 3.5 to 4.5, 4.0 to 4.5 or is about 4.2.

In a further aspect of the invention the hydrolysis step is conducted until 70% or more, 80% or more, 85% or more, 90% or more, 92% or more, 95% or more of available sugar in the lignocellulosic material is released.

Significantly, a process of the invention may be carried out using high levels of dry matter (of the lignocellulosic material) in the hydrolysis reaction. Thus, the invention may be carried out with a dry matter content of about 5 wt % or higher, about 8 wt % or higher, about 10 wt % or higher, about 11 wt % or higher, about 12 wt % or higher, about 13 wt % or higher, about 14 wt % or higher, about 15 wt % or higher, about 20 wt % or higher, about 25 wt % or higher, about 30 wt % or higher, about 35 wt % or higher or about 40 wt % or higher. In a further embodiment, the dry matter content in the hydrolysis step is 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt % or more or 14 to 33 wt %.

In another embodiment the dry matter content at the end of the hydrolysis is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher or 39 wt % or higher. In another embodiment the dry matter content at the end of the enzymatic hydrolysis is between 5 wt %-40 wt %, 6 wt %-40 wt %, 7 wt %-40 wt %, 8 wt %-40 wt %, 9 wt %-40 wt %, 10 wt %-40 wt %, 11 wt %-40 wt %, 12 wt %-40 wt %, 13 wt %-40 wt %, 14 wt %-40 wt %, 15 wt %-40 wt %, 16 wt %-40 wt %, 17 wt %-40 wt %, 18 wt %-40 wt %, 19 wt %-40 wt %, 20 wt %-40 wt %, 21 wt %-40 wt %, 22 wt %-40 wt %, 23 wt %-40 wt %, 24 wt %-40 wt %, 25 wt %-40 wt %, 26 wt %-40 wt %, 27 wt %-40 wt %, 28 wt %-40 wt %, 29 wt %-40 wt %, 30 wt %-40 wt %, 31 wt %-40 wt %, 32 wt %-40 wt %, 33 wt %-40 wt %, 34 wt %-40 wt %, 35 wt %-40 wt %, 36 wt %-40 wt %, 37 wt %-40 wt %, 38 wt %-40 wt %, 39 wt %-40 wt %.

Fermentation

The process according to the invention may comprise a fermentation step. The fermentation can be done simultaneously with the hydrolysis in one reactor (SSF). Preferably the fermentation is done after the hydrolysis and optimal conditions for both hydrolysis and fermentation can be selected which might be different for hydrolysis and fermentation. In a further aspect, the invention thus includes in step fermentation processes in which a microorganism is used for the fermentation of a carbon source comprising sugar(s), e.g. glucose, L-arabinose and/or xylose. The carbon source may include any carbohydrate oligo- or polymer comprising L-arabinose, xylose or glucose units, such as e.g. lignocellulose, xylans, cellulose, starch, arabinan and the like. For release of xylose or glucose units from such carbohydrates, appropriate carbohydrases (such as xylanases, glucanases, amylases and the like) may be added to the fermentation medium or may be produced by the modified host cell. In the latter case the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose. In a preferred process the modified host cell ferments both the L-arabinose (optionally xylose) and glucose, preferably simultaneously in which case preferably a modified host cell is used which is insensitive to glucose repression to prevent diauxic growth. In addition to a source of L-arabinose, optionally xylose (and glucose) as carbon source, the fermentation medium will further comprise the appropriate ingredient required for growth of the modified host cell. Compositions of fermentation media for growth of microorganisms such as yeasts or filamentous fungi are well known in the art.

The fermentation time may be shorter than in conventional fermentation at the same conditions, wherein part of the enzymatic hydrolysis still has to take part during fermentation. In one embodiment, the fermentation time is 100 hours or less, 90 hours or less, 80 hours or less, 70 hours or less, or 60 hours or less, for a sugar composition of 50 g/l glucose and corresponding other sugars from the lignocellulosic feedstock (e.g. 50 g/l xylose, 35 g/l L-arabinose and 10 g/l galactose. For more dilute sugar compositions the fermentation time may correspondingly be reduced.

The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$. Thus, in a preferred anaerobic fermentation process pyruvate is used as an electron (and hydrogen acceptor) and is reduced to fermentation products such as ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotics and a cephalosporin. In a preferred embodiment, the fermentation process is anaerobic. An anaerobic process is advantageous since it is cheaper than aerobic processes: less special equipment is needed. Furthermore, anaerobic processes are expected to give a higher product yield than aerobic processes. Under aerobic conditions, usually the biomass yield is higher than under anaerobic conditions. As a consequence, usually under aerobic conditions, the expected product yield is lower than under anaerobic conditions.

In another embodiment, the fermentation process is under oxygen-limited conditions. More preferably, the fermentation process is aerobic and under oxygen-limited conditions. An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used. Preferably, in a process under oxygen-limited conditions, the rate of oxygen consumption is at least 5.5, more preferably at least 6 and even more preferably at least 7 mmol/L/h.

The fermentation process is preferably run at a temperature that is optimal for the modified cell. Thus, for most yeasts or fungal cells, the fermentation process is performed at a temperature which is less than 42° C., preferably less than 38° C. For yeast or filamentous fungal host cells, the fermentation process is preferably performed at a temperature which is lower than 35, 33, 30 or 28° C. and at a temperature which is higher than 20, 22, or 25° C.

In an embodiment of the invention, in step the fermentation is conducted with a microorganism that is able to ferment at least one C5 sugar. In an embodiment the process is a process for the production of ethanol whereby the process comprises the step comprises fermenting a medium containing sugar(s) with a microorganism that is able to ferment at least one C5 sugar, whereby the host cell is able to ferment glucose, L-arabinose and xylose to ethanol. The microorganism may be a prokaryotic or eukaryotic organism. The microorganism used in the process may be a genetically engineered microorganism. Examples of suitable organisms are yeasts, for instance *Saccharomyces*, e.g. *Saccharomyces cerevisiae, Saccharomyces pastorianus* or *Saccharomyces uvarum, Hansenula, Issatchenkia*, e.g. *Issatchenkia orientalis, Pichia*, e.g. *Pichia stipites* or *Pichia pastoris, Kluyveromyces*, e.g. *Kluyveromyces fagilis, Candida*, e.g. *Candida pseudotropicalis* or *Candida acidothermophilum, Pachysolen*, e.g. *Pachysolen tannophilus* or bacteria, for instance *Lactobacillus*, e.g. *Lactobacillus lactis, Geobacillus, Zymomonas*, e.g. *Zymomonas mobilis, Clostridium*, e.g. *Clostridium phytofermentans, Escherichia*, e.g. *E. coli, Klebsiella*, e.g. *Klebsiella oxytoca*. In an embodiment thereof the microorganism that is able to ferment at least one C5 sugar is a yeast. In an embodiment, the yeast is belongs to the genus *Saccharomyces*, preferably of the species *Saccharomyces cerevisiae*, in which genetic modifications have been made. An example of such a microorganism and its preparation is described in more detail in WO 2008/041840 and in European Patent Application EP10160622.6, filed 21 Apr. 2010. In an embodiment, the fermentation process for the production of ethanol is anaerobic. Anaerobic has already been defined earlier herein. In another preferred embodiment, the fermentation process for the production of ethanol is aerobic. In another preferred embodiment, the fermentation process for the production of ethanol is under oxygen-limited conditions, more preferably aerobic and under oxygen-limited conditions. Oxygen-limited conditions have already been defined earlier herein.

In such process, the volumetric ethanol productivity is preferably at least 0.5, 1.0, 1.5, 2.0, 2.5, 3.0, 5.0 or 10.0 g ethanol per litre per hour. The ethanol yield on L-arabinose and optionally xylose and/or glucose in the process preferably is at least 20, 25, 30, 35, 40, 45, 50, 60, 70, 80, 90, 95 or 98%. The ethanol yield is herein defined as a percentage of the theoretical maximum yield, which, for glucose and L-arabinose and optionally xylose is 0.51 g. ethanol per g. glucose or xylose.

In one aspect the fermentation process leading to the production of ethanol has several advantages by comparison to known ethanol fermentations processes:
 anaerobic processes are possible;
 oxygen limited conditions are also possible;
 higher ethanol yields and ethanol production rates can be obtained;
 the strain used may be able to use L-arabinose and optionally xylose.

Alternatively to the fermentation processes described above, at least two distinct cells may be used, this means this process is a co-fermentation process. All preferred embodiments of the fermentation processes as described above are also preferred embodiments of this co-fermentation process: identity of the fermentation product, identity of source of L-arabinose and source of xylose, conditions of fermentation (aerobic or anaerobic conditions, oxygen-limited conditions, temperature at which the process is being carried out, productivity of ethanol, yield of ethanol).

The fermentation process may be carried out without any requirement to adjust the pH during the process. That is to say, the process is one which may be carried out without the addition of any acid(s) or base(s). However, this excludes a pretreatment step, where acid may be added. The point is that the composition of the invention is capable of acting at low pH and, therefore, there is no need to adjust the pH of acid of an acid pretreated feedstock in order that saccharification or hydrolysis may take place. Accordingly, a method of the invention may be a zero waste method using only organic products with no requirement for inorganic chemical input.

Overall Reaction Time

According to the invention, the overall reaction time (or the reaction time of hydrolysis step and fermentation step together) may be reduced. In one embodiment, the overall reaction time is 300 hours or less, 200 hours or less, 150 hours or less, 140 hours or less, 130 or less, 120 hours or less, 110 hours or less, 100 hours of less, 90 hours or less, 80 hours or less, 75 hours or less, or about 72 hours at 90% glucose yield. Correspondingly lower overall times may be reached at lower glucose yield.

Fermentation Products

Fermentation products which may be produced according to the invention include amino acids, vitamins, pharmaceuticals, animal feed supplements, specialty chemicals, chemical feedstocks, plastics, solvents, fuels, or other organic polymers, lactic acid, and ethanol, including fuel ethanol (the term "ethanol" being understood to include ethyl alcohol or mixtures of ethyl alcohol and water).

Specific value-added products that may be produced by the methods of the invention include, but not limited to, biofuels (including biogas, ethanol and butanol); lactic acid; 3-hydroxy-propionic acid; acrylic acid; acetic acid; 1,3-propane-diol; ethylene; glycerol; a plastic; a specialty chemical; an organic acid, including citric acid, succinic acid and maleic acid; a solvent; an animal feed supplement; a pharmaceutical such as a β-lactam antibiotic or a cephalosporin; a vitamin; an amino acid, such as lysine, methionine, tryptophan, threonine, and aspartic acid; an enzyme, such as a protease, a cellulase, an amylase, a glucanase, a lactase, a lipase, a lyase, an oxidoreductase, a transferase or a xylanase; a chemical feedstock; or an animal feed supplement.

Fermentation products that may be produced by the processes of the invention can be any substance derived from fermentation, They include, but are not limited to, alcohols (such as arabinitol, butanol, ethanol, glycerol, methanol, 1,3-propanediol, sorbitol, and xylitol); organic acid (such as acetic acid, acetonic acid, adipic acid, ascorbic acid, acrylic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, maleic acid, malic acid, malonic acid, oxalic acid, oxaloacetic acid, propionic acid, succinic acid, and xylonic acid); ketones (such as acetone); amino acids (such as aspartic acid, glutamic acid, glycine, lysine, serine, tryptophan, and threonine); alkanes (such as pentane, hexane, heptane, octane, nonane, decane, undecane, and dodecane), cycloalkanes (such as cyclopentane, cyclohexane, cycloheptane, and cyclooctane), alkenes (such as pentene, hexene, heptene, and octene); and gases (such as methane, hydrogen ($H_2$), carbon dioxide ($CO_2$), and carbon monoxide (CO)). The fermentation product can also be a protein, a vitamin, a pharmaceutical, an animal feed supplement, a specialty chemical, a chemical feedstock, a plastic, a solvent, ethylene, an enzyme, such as a protease, a cellulase, an amylase, a glucanase, a lactase, a lipase, a lyase, an oxidoreductase, a transferase or a xylanase.

Separation of Fermentation Product

The process according to the invention optionally comprises recovery of fermentation product. A fermentation product may be separated from the fermentation broth in any known manner. For each fermentation product the skilled person will thus be able to select a proper separation technique. For instance ethanol may be separated from a yeast fermentation broth by distillation, for instance steam distillation/vacuum distillation in conventional way.

Certain embodiments of the invention will below be described in more detail, but are in no way limiting the scope of the present invention.

Use of Thermostable Enzymes Under Optimal Temperature Conditions

In one embodiment, the invention relates to the use of thermostable enzymes such as cellulolytic enzymes of *Rasamsonia* for the production of reducing sugars from pre-treated lignocellulosic feedstock in, but not limiting to, ethanol production. Cellulolytic enzymes of *Rasamsonia* applied on pre-treated lignocellulosic feedstock showed maximal conversion rates at temperature within the range of 50 to 70° C. The enzyme remains active under these circumstances for 14 days and more without complete cessation of activity.

By using optimal temperature conditions, maximal amount of reducing sugars can be released from feedstock (total hydrolysis) within the shortest possible hydrolysis time. In this way, 100% conversion of cellulose in glucose is achieved in less than 5 days.

The theoretical maximum yield (Yps max in g product per gram glucose) of a fermentation product can be derived from textbook biochemistry. For ethanol, 1 mole of glucose (180 g) yields according to normal glycolysis fermentation pathway in yeast 2 moles of ethanol (=2×46=92 g ethanol. The theoretical maximum yield of ethanol on glucose is therefore 92/180=0.511 g ethanol/g glucose.

For butanol (MW 74 g/mole) or iso butanol, the theoretical maximum yield is 1 mole of butanol per mole of glucose. So Yps max for (iso-)butanol=74/180=0.411 g (iso-) butanol/g glucose.

For lactic acid the fermentation yield for homolactic fermentation is 2 moles of lactic acid (MW=90 g/mole) per mole of glucose. According to this stoichiometry, the Yps max=1 g lactic acid/g glucose.

For other fermentation products a similar calculation may be made.

The cost reduction achieved with applying cellulolytic enzymes of *Rasamsonia* will be the result of an overall process time reduction.

Compensation of Lower Enzyme Dosage with Extended Hydrolysis Time Using *Rasamsonia* Enzymes Due to the high stability of the stable enzymes, the activities do not cease in time, although less reducing sugars are liberated in the course of the hydrolysis. It is possible to lower the enzyme dosage and extend the use of the enzyme by prolonging the hydrolysis times to obtain similar levels of released reducing sugars. For example, 0.175 mL enzyme/g feedstock dry-matter resulted in release of approximately 90% of the theoretical maximum of reducing sugars from pre-treated feedstock within 72 h. When using 0.075 mL enzyme/g feedstock dry-matter, approximately 90% conversion of the theoretical maximum is achieved within 120 h. The results show that, because of the stability of the enzyme activity, lowering the enzyme dosage can be compensated by extending the hydrolysis time to obtain the same amount of reducing sugars. The same holds for hydrolysis of pre-treated feedstock at dry-matter contents higher than 10% shows that compensating effect of extended hydrolysis time at 15% dry matter feedstock.

The cost reduction achieved by using stable cellulolytic enzymes, such as of *Rasamsonia*, results from requiring less enzyme dosage, resulting in similar hydrolysis conversion yields.

Lowering the Risk on Contamination with Stable Enzymes

In a common process for converting lignocellulosic material into ethanol, process steps are preferably done under septic conditions to lower the operational costs. Contamination and growth of contaminating microorganisms can therefore occur and result in undesirable side effects, such lactic acid, formic acid and acetic acid production, yield losses of ethanol on substrate, production of toxins and extracellular polysaccharides, which may affect production costs significantly. A high process temperature and/or a short process time will limit the risk on contamination during hydrolysis and fermentation. Thermostable enzymes, like those of *Rasamsonia*, are capable of hydrolysing lignocellulosic feedstock at temperatures of higher than 60° C. At these temperatures, the risk that a contaminating microorganism will cause undesired side effects will be little to almost zero.

During the fermentation step, in which ethanol is produced, temperatures are typically between 30 to 37° C. and will preferably not be raised because of production losses. By applying fermentation process times as short as possible the risks and effects of contamination and/or growth of contaminants will be reduced as much as possible. With stable enzymes, like those of *Rasamsonia*, a short as possible fermentation times can be applied (see description above), and thus risks on contamination and/or growth of contaminants will be reduced as much as possible. The cost reduction achieved with applying thermostable cellulolytic enzymes of *Rasamsonia* in this way will result from lower risk of process failures due to contamination.

Stable Enzymes Reduce Cooling Costs and Increase Productivity of Ethanol Plants

The first step after thermal pretreatment will be to cool the pretreated feedstock to temperatures where the enzymes are optimal active. On large scale, this is typically done by adding (cooled) water, which will, besides decreasing the temperature, reduce the dry-matter content. By using thermos stable enzymes, like those of *Rasamsonia*, cost reduction can be achieved by the fact that (i) less cooling of the pretreated feedstock is required since higher temperatures are allowed during hydrolysis, and (ii) less water will be added, which will increase the dry-matter content during hydrolysis and fermentation and thus increase the ethanol production capacity (amount produced per time unit per volume) of an ethanol plant. Also, by using thermostable enzymes according to the invention, like those of *Rasamsonia*, cost reduction may also be achieved by using cooling water having higher temperature that the water that is used in a process with non-thermostable enzyme.

Enzyme Recycling after Hydrolysis with Stable Enzymes

At the end of the hydrolysis, enzyme activities appear to be low since little reducing sugars are released once almost all cellulose is converted. The amount of enzymatic activity present, however, has decreased only a little, assumingly mainly due to absorption of the enzymes to the substrate. By applying solid-liquid separation after hydrolysis, such as centrifugation, filtration, sedicantation, etcetera, 60% or more e.g. 70% of the enzyme activity in solution can be recovered and re-used for hydrolysis of a new pre-treated lignocellulosic feedstock during the next hydrolysis.

Moreover, after solid-liquid separation the enzyme in solution can be separated from the solution containing reducing sugars and other hydrolysis products from the enzymatic actions. This separation can be done by, but not limiting to, (ultra and micro)filtration, centrifugation, sedicantation, sedimentation, with or without first adsorption of the enzyme to a carrier of any kind.

For example, after hydrolysis of pre-treated feedstock with 0.175 mL/g feedstock dry matter enzyme load for 20 h, 50% of the theoretical maximum amount of reducing sugars is liberated and after the same hydrolysis for 72 h, 90% of the theoretical maximum amount of reducing sugars is liberated. By centrifugation and ultrafiltration, 60-70% of the enzyme activity was recovered in the retentate, while the filtrate contained more than 80% of the liberated reducing sugars. By re-using the retentate, either as it is or after further purification and/or concentration, enzyme dosage during the next hydrolysis step can be reduced with 60 to 70%. The cost reduction achieved by using stable cellulolytic enzymes, such as of *Rasamsonia*, in this way results from requiring less enzyme dosage.

Enzyme Recycling after Hydrolysis in Combination with Enzyme Production and Yeast-Cell Recycling With Stable Enzymes The process including enzyme recycling after hydrolysis, as described above, can be combined with recycling of the ethanol producing microorganism after fermentation and with the use of the reducing sugars containing filtrate as a substrate (purified and/or concentrated or diluted) in enzyme-production fermentation and as substrate for the cultivation of the ethanol-producing microorganism.

Enzyme Recycling after Vacuum Distillation with Stable Enzymes

The thermo stability of enzymes, like those from *Rasamsonia*, causes remaining cellulolytic activity after hydrolysis, fermentation and vacuum distillation in the thin stillage. The total activity of the enzyme is reduced during the three successive process steps. The thin stillage obtained after vacuum distillation can thus be re-used as a source of enzyme for a newly started hydrolysis-fermentation-distillation process cycle of pre-treated wheat straw conversion into ethanol. The thin stillage can be used either in concentrated or (un)diluted form and/or purified and with or without additional enzyme supplementation.

Enzyme Recycling in Combination with Enzyme Supplementation after Vacuum Distillation with Thermostable Enzymes In an optimal process, an amount of enzyme is supplemented into the thin stillage, before its re-use in a new process cycle, equal to the amount of activity lost during the three successive process steps of the previous process cycle. In this way over-dosage of enzyme is avoided and thus most efficient use of enzyme is obtained.

Moreover, by providing high enzyme dosage in the first process cycle, and supplementing enzyme equal to the amount of activity lost during the three successive process steps in the following process cycles, highest possible hydrolysis rates can be obtained in each process cycle resulting in short hydrolysis times of less than 48 h in combination with most efficient use of enzymes.

Use of Stable Enzymes in Mixed Systems

By applying mixing during hydrolysis, enzymes come more often in contact with substrates, which results in a more efficient use of the catalytic activity. This will result in a lower enzyme dosages and thus in lower costs, unless the mixing has a negative effect on the enzymes. Stable enzymes, like the thermostable enzymes from *Rasamsonia*, are robust and can resist circumstances of (locally) high shear and temperatures, which is the case during intensive mixing of slurries. The use of it in mixed systems is therefore beneficial and will lead to dosage and thus costs reduction.

The invention is further described by the following examples, which should not be construed as limiting the scope of the invention.

EXAMPLES

Experimental Information
Strains

Suitable *Rasamsonia* strains that can be used in the present examples to show the effect and advantages of the invention are for example TEC-101, TEC-147, TEC-192, TEC-201 or TEC-210. The strains are described in WO 2011/000949.

Preparation of Acid Pre-Treated Corn Stover Substrate

Dilute-acid pre-treated corn stover (aCS) was obtained as described in Schell, D. J., Applied Biochemistry and Biotechnology (2003), vol. 105-108, pp 69-85. A pilot scale pretreatment reactor was used operating at steady state conditions of 190° C., 1 min residence time and an effective $H_2SO_4$ acid concentration of 1.45% (w/w) in the liquid phase.

Protein Measurement Assays
1. Total Protein
TCA Biuret

The method was a combination of precipitation of protein using trichloro acetic acid (TCA) to remove disturbing substances and allow determination of the protein concentration with the colorimetric Biuret reaction. In the Biuret reaction, a copper (II) ion is reduced to copper (I), which forms a complex with the nitrogens and carbons of the peptide bonds in an alkaline solution. A violet color indicates the presence of proteins. The intensity of the color, and hence the absorption at 546 nm, is directly proportional to the protein concentration, according to the Beer-Lambert law. The standardisation was performed using BSA (Bovine Serum Albumine) and the protein content was expressed in g protein as BSA equivalent/L or mg protein as BSA equivalent/ml. The protein content was calculated using standard calculation protocols known in the art, by plotting the $OD_{546}$ versus the concentration of samples with known concentration, followed by the calculation of the concentration of the unknown samples using the equation generated from the calibration line.

2. Individual Proteins Using PAGE
Sample Pretreatment SDS-PAGE

Based on the estimated protein concentration of the samples the following samples preparation was performed. To 10 μl sample 40 μl MilliQ water and 50 μl TCA (20%) was added to dilute the sample five times (~1 mg/ml) and precipitate the proteins. After 1 hour on ice the sample was centrifuged (10 minutes, 14000 rpm). The pellet was washed with 500 μl aceton and centrifuged (10 minutes, 14000 rpm). The pellet was treated as described below.

SDS-PAGE

The pellet was dissolved in 65 μl of the MilliQ water, 25 μl NuPAGE™ LDS sample buffer (4×) Invitrogen and 10 μl NuPAGE™ Sample Reducing agent (10×) Invitrogen. Prior to the the deanuarion step the sample was diluted 5 times using a mix of MilliQ; NuPAGE™ LDS sample buffer and 10 μl NuPAGE™ Sample Reducing in the ratio of 65:25:10. After mixing, the samples were incubated in a thermo mixer for 10 minutes at 70° C. The sample solutions were applied on a 4-12% Bis-Tris gel (NuPAGE™ BisTris, Invitrogen). A sample (10 μl) of marker M12 (Invitrogen) was also applied on the gel. The gel was run at 200 V for 50 minutes, using the XCELL Surelock, with 600 ml 20× diluted SDS buffer in the outer buffer chamber and 200 ml 20×diluted SDS buffer, containing 0.5 ml of antioxidant (NuPAGE™ Invitrogen) in the inner buffer chamber. After running, the gel was rinsed twice with demineralised water the gels were fixed with 50% methanol/7% acetic acid solution for one hour and stained with Sypro Ruby (50 ml per gel) overnight. An image was made using the Typhoon 9200 (610 BP 30, Green (532 nm), PMT 600V, 100 micron) after washing the gel with MilliQ water.

Quantitative Analysis of the Protein

Using the Typhoon scanner the ratio between protein bands within a lane was determined using standard methods known in the art. The sample was applied in triplicate and the gray values were determined using the program Image quant. Values are expressed as relative % protein to the total protein, calculated using the gray value of the selected protein band relative to the total gray value all the protein bands.

glucan conversion (%)=(glucose (g/l)×100%)/(glucan (fraction on DM)×dm (g/kg)×1.1)Glucan Conversion Calculation:

Wherein:

glucose (g/l)=glucose concentration in supernatant after hydrolysis.

glucan (fraction on dm)=glucan content of the substrate before pretreatment.

dm (g/kg)=dry matter of hydrolysis (f.i. 20% dm=200 g/kg).

1.1=weight increase due to water incorporation during hydrolysis.

Example Calculation:

glucose=60 g/l glucan fraction=0.40 (is 40% on dry matter)

dm=200 g/kg glucan conversion example=(60*100)/(0.4×200×1.1)
=68% conversion

Correction for evaporation is made if necessary. The concentration in the supernatant is subsequently converted to the concentration per kg hydrolysate.

Measurement of Gluconic Acid in Biomass Hydrolysates by UPLC-MS/MS

The assay is based on separation of gluconic acid with an UPLC column and detection by means of MS/MS (based on negative electrospray ionization). In order to exclude errors caused by ion suppression, evaporation and injection effects, a labelled internal standard, namely $^{13}C_6$-gluconic acid, is used.

Chemicals and Reference Compounds

Water used for sample preparation and UPLC-MS/MS analysis was filtered by a Millipore 0.22 µm filter. HPLC-grade acetonitrile was obtained from Merck (Amsterdam, the Netherlands). 0.1% (v/v) formic acid in water and 0.1% formic acid in acetonitrile were obtained from Biosolve B.V. (Valkenswaard, the Netherlands). Gluconic acid reference compound was obtained from Sigma (Zwijndrecht, the Netherlands). Isotopically labelled gluconic acid ($^{13}C_6$, used as internal standard) was custom made by Buchem B.V. (Apeldoorn, the Netherlands).

Internal Standard Solution

A stock solution was made by weighing 10 mg $^{13}C_6$-gluconic acid in a 10 mL volumetric flask and dissolving in 10 mL water (~1 mg/mL). From this stock solution a working solution was prepared by pipetting 100 µL of the internal standard stock solution and adding 9.99 mL water (c~10 µg/mL).

Standard Solutions

A stock solution of gluconic acid was made by weighing 5 mg gluconic acid and adding 10 mL water. The stock solution was further diluted by pipetting 20 µL of the stock solution and adding 980 µL water (dilution 1, c~10 µg/mL). A further dilution was made by pipetting 100 µL of dilution 1 and adding 900 µL water (dilution 2, c~1 µg/mL). A calibration curve was made in HPLC vials according to Table 1 below.

Sample Preparation

Biomass hydrolysates were defrosted, if necessary, and diluted ten times with water by diluting 150 µL of sample in a Eppendorf vial with 1350 µL water followed by centrifugation at 13000 rcf for 15 minutes. The resulting supernatant was diluted fifty times with water by pipetting 20 µL of supernatant in a HPLC vial and adding 100 µL internal standard working solution and 880 µL water.

UPLC-MS/MS

Gluconic acid was analyzed on a Waters UPLC iClass system consisting of a Waters iClass Binary Solvent Manager and a Water iClass Sample Manager FTN connected to a Waters Xevo TQD mass spectrometer (Waters, Milford, Mass., USA). Chromatographic separation was achieved with a Waters Acquity UPLC BEH C18 column (150×2.1 mm, 1.8 µm) using a gradient elution with A) 0.1% (v/v) formic acid in water and B) 0.1% formic acid in acetonitrile as mobile phases. The 7 min gradient started with 1 minute at 99% A followed by a linear decrease to 90% A in 2 minutes, then washing with 20% A for 2 minutes and re-equilibrating with 99% A for 2 minutes. The flow rate was kept at 0.35 mL/min, using an injection volume of 5 µl and the column temperature was set to 40° C.

The mass spectrometer was operated in the negative ionization mode. Data acquisition and peak integration were performed with Masslynx 4.1 software (Waters). Gluconic acid and $^{13}C_6$-gluconic acid detection was performed in multiple reaction monitoring mode (MRM). The general settings were as follows: the ESI capillary voltage was 2.0 kV, extractor voltage 3.0 V, cone voltage 30 V. The desolvation gas (nitrogen) flow was 800 L/h with the temperature set at 350° C., the cone gas (nitrogen) flow was 50 L/h, and the source temperature was 150° C. The following MRM settings were used: gluconic acid m/z 195.0→129.0, dwell time 0.1 s, collision voltage 2 V; $^{13}C_6$-gluconic acid m/z 201.0→134.0, dwell time 0.08 s, collision voltage 2 V.

Quantification

The concentration of gluconic acid in g/L was calculated using linear regression:

$$g/l\ compound = \frac{((Area\ compound/Area\ internal\ standard) - intercept) * 1000 \cdot (dilution\ factor)}{Slope\ of\ calibration\ line * 1000}$$

The calculated amount gluconic acid in g/l can be converted into gluconic acid in g/kg glucan in the lignocellulosic material by means of the following calculation.

When using acid pretreated corn stover at a concentration of 20% (w/w) dm, at the end of hydrolysis for 120 hours, at pH 4.5 and 62° C. there is a pellet volume of 6% (due to insoluble) and a supernatant volume of 94%. The supernatant has a density of 1.07 kg/l and a glucan percentage of 36%. So, acid pretreated corn stover at a concentration of 20% (w/w) dm has 72 g glucan/kg hydrolysate.

Starting with, for instance, 0.5 g/l gluconic acid this gives 0.5/1.07=0.47 g gluconic acid/kg supernatant (1.07 is density of liquid). This corresponds with 0.47*0.94=0.44 g gluconic acid/kg hydrolysate (pellet factor is 6% due to insoluble). When using acid pretreated corn stover at a concentration of 20% (w/w) dm, this corresponds with 0.44/0.072=6.1 g gluconic acid/kg glucan.

Example 1

Use of Oxygen During Hydrolysis to Control the Amount of Gluconic Acid Formed

Optimal enzymatic hydrolysis of pretreated cornstover having 20% dry matter (containing 36% glucan on dry matter) at a reactor temperature of 60° C. and pH of 4.5 is obtained by keeping the gluconic acid concentration between 0.7 and 1.5 g/l in the supernatant of the hydrolysate by the addition of oxygen. This corresponds to 9.7-20.8 g gluconic acid produced per kg glucan during the hydrolysis of glucan. The hydrolysis is performed with 2.5 mg/g dry matter feedstock of TEC-210 cellulase enzyme composition (or cocktail). TEC-210 is produced according to the inoculation and fermentation procedures described in WO 2011/000949.

Example 2

Use of Oxygen During Hydrolysis to Control the Amount of Gluconic Acid Formed

The enzymatic hydrolysis was performed using acid pretreated cornstover (aCS) feedstock at a concentration of 20% (w/w) dry matter (dm). The feedstock solution was prepared by the dilution of concentrated feedstock slurry with water. The pH was adjusted to pH 4.5 with a 25% (w/w) $NH_4OH$-solution. The enzymatic hydrolysis was performed at 1 kg scale using a 1.5 liter reactor. The pH was controlled at 4.5 and the temperature was controlled at 62° C. The dissolved oxygen during the process was controlled by headspace gas recycling and additional fresh air (containing 20-21% oxygen).

Prior to enzyme addition, headspace gas was recylced at a gas flow of 3 l/hour using a peristaltic pump and a sparger. Due to the fact that the feedstock consumes oxygen through a chemical reaction, the DO level reached a level of 0% DO within one hour resulting in an anaerobic feedstock and a headspace which was completely depleted from oxygen. The resulting inert headspace gas (oxygen-free) was used throughout the entire hydrolysis as carrier gas for the introduced fresh air.

Next, the cellulase enzyme cocktail TEC210 was added to the feedstock at a dosage of 3.75 mg (TCA protein)/g dm. TEC-210 was produced according to the inoculation and fermentation procedures described in WO 2011/000949. The total hydrolysis time was 120 hours.

Fresh air was introduced into the recycle loop of inert headspace gas during the entire hydrolysis process at a fresh air flow of 0-3-6-12-24 or 48 ml per kg reaction mixture per hour, respectively, starting directly after enzyme addition. The DO was measured constantly in all experiments. Samples were drawn at the start and end of the experiment for glucose analysis by HPLC.

A parallel experiment was conducted in a shake flask to determine the maximum level of glucan hydrolysis. This maximum hydrolysis was determined by incubating the feedstock at a very high enzyme dosage (50 mg (TCA protein)/g dm) at similar conditions (pH, temperature and dm) in a surplus of oxygen containing headspace air. DO measurement in each experiment constantly showed 0% DO. This can be explained by direct consumption of oxygen after its transfer from the oxygen containing recycle gas stream into the liquid phase in the reactor.

The results are presented in Table 2. The glucose production increase is calculated by subtracting the glucose concentration (in g/l) at the start of the hydrolysis from the glucose concentration (in g/l) at the end of the hydrolysis for each condition (i.e. fresh air flow (ml/kg/h) 0-3-6-12-24-48-96) and dividing the respective values with the value found when the fresh air flow (ml/kg/h) is 0 (this value was set to be 100%).

The data clearly demonstrate that higher amounts of glucose are formed when the amount of formed gluconic acid at the end of the hydrolysis is kept above 3 g/kg glucan in the lignocellulosic material.

Example 3

The Effect of Gluconic Acid on Enzymatic Hydrolysis of Lignocellulosic Feedstock Twenty grams of pretreated corn stover were incubated in a 50 ml Greiner test tube for 50 hours at a dry matter level of 6% w/w, pH 4.5 at 62° C. in the presence of 5 mg of the cellulase enzyme cocktail TEC210 per gram of dry matter and in the presence of 0, 2, 4, 6, or 8 g/l gluconic acid to determine the inhibiting effect of gluconic acid on the hydrolysis of glucan in lignocellulosic feedstock. The experiment is performed at maximum oxygen saturation.

Samples were taken after 50 hours of incubation and the samples were centrifuged for further analysis in an Eppendorf centrifuge type 5810 for 8 minutes at 4000 rpm. The glucose concentration was measured in the supernatant of each sample by means of HPLC using a Bio-Rad HPX87H column. The results are shown in Table 3. The glucose release as presented in Table 3 is a direct measure for the enzymatic hydrolysis (glucan hydrolysis). A gluconic acid level of 2 g/l in the supernatant corresponds with 89 g/kg glucan in the lignocellulosic material. This can be calculated as described above with a density of 1.02 kg/l, a pellet factor of 2% and a glucan content of 21.6 g glucan/kg hydrolysate.

The results clearly indicate that higher concentrations of gluconic acid have a negative effect on glucan hydrolysis.

TABLE 1

| | Calibration curve | | | | |
|---|---|---|---|---|---|
| Standard | Final concentration (μg/mL) | μL standard solution dilution 1 | μL standard solution dilution 2 | μL internal standard working solution | μL water |
| Std 1 | ~0.1 | | | 100 | 100 | 800 |
| Std 2 | ~0.2 | | 200 | 100 | 700 |
| Std 3 | ~0.5 | 50 | | 100 | 850 |
| Std 4 | ~1 | 100 | | 100 | 800 |
| Std 5 | ~2 | 200 | | 100 | 700 |
| Std 6 | ~5 | 500 | | 100 | 400 |

TABLE 2

The effect of addition of oxygen in the enzymatic hydrolysis of lignocellulosic feedstock.

| Fresh air flow (in ml/kg/h) | Amount of oxygen (introduced through fresh air in mmol/kg glucan/hour)* | Gluconic acid (in g/kg glucan in lignocellulosic material) | Glucose production increase (in %) |
|---|---|---|---|
| 0 | 0 | 2.96 | — |
| 3 | 0.36 | 3.33 | 12.5 |
| 6 | 0.72 | 3.82 | 34 |
| 12 | 1.43 | 3.82 | 31 |
| 24 | 2.86 | 4.93 | 28 |
| 48 | 5.71 | 6.40 | 41 |
| 96 | 11.42 | 8.99 | 53 |

*Oxygen = 24.5 l/mol at 25° C. and glucan content is 72 g/kg hydrolysate

TABLE 3

The effect of gluconic acid on enzymatic hydrolysis.

| Gluconic acid added (in g/l) | Gluconic acid (in g/kg glucan in lignocellulosic material) | Glucose release (in %) |
|---|---|---|
| 0 | 0 | 100 |
| 2 | 89 | 90 |
| 4 | 178 | 82 |
| 6 | 267 | 79 |
| 8 | 356 | 77 |

The invention claimed is:

1. A process for preparation of a sugar product from lignocellulosic material, comprising:

optionally, pretreatment of the lignocellulosic material;

optionally, washing of the optionally pretreated lignocellulosic material;

enzymatic hydrolysis of the lignocellulosic material, the optionally washed and/or the optionally pretreated lignocellulosic material in the presence of an enzyme composition comprising at least two cellulases and at least a lytic polysaccharide monooxygenase (LPMO);

adding 20-10,000 mmol of oxygen per kg glucan to the lignocellulosic material during the enzymatic hydrolysis; and optionally, recovery of a glucose-containing composition; thereby producing the sugar product;

wherein at the end of the enzymatic hydrolysis the amount of gluconic acid formed during oxidation of the lignocellulosic material is kept between 3 to 10 g/kg glucan present in the lignocellulosic material.

2. A process for preparation of a fermentation product from lignocellulosic material, comprising:

optionally, pretreatment of the lignocellulosic material;

optionally, washing of the optionally pretreated lignocellulosic material;

enzymatic hydrolysis of the lignocellulosic material, the optionally washed and/or the optionally pretreated lignocellulosic material in the presence of an enzyme composition comprising at least two cellulases at least a lytic polysaccharide monooxygenase (LPMO), and optionally purifying the hydrolysed lignocellulosic material;

adding 20-10,000 mmol of oxygen per kg glucan to the lignocellulosic material during the enzymatic hydrolysis;

fermentation of the hydrolysed lignocellulosic material to produce the fermentation product; and optionally, recovery of a fermentation product;

wherein at the end of the enzymatic hydrolysis the amount of gluconic acid formed during oxidation of the lignocellulosic material is kept between 3 to 10 g/kg glucan present in the lignocellulosic material.

3. The process of claim 2, wherein the fermentation is conducted with a microorganism that is able to ferment at least one C5 sugar.

4. The process of claim 3, wherein the microorganism is a genetically modified *Saccharomyces cerevisiae*.

5. The process of claim 1, wherein the oxygen is added in the form of bubbles.

6. The process of claim 1, wherein the enzymatic hydrolysis is in a reactor with a volume of 1 m³ or more.

7. The process of claim 1, wherein the enzymatic hydryolysis time is 5 to 150 hours.

8. The process of claim 1, wherein the enzyme composition retains activity for 30 hours or more.

9. The process of claim 1, wherein the hydrolysis is conducted at a temperature of 45° C. or more.

10. The process of claim 1, wherein the enzyme composition comprises a fungal enzyme.

11. The process of claim 1, wherein the dry matter content in the enzymatic hydrolysis step is 10 wt % or more.

12. The process of claim 1, in which the enzymatic hydrolysis takes place in a batch, fed batch and/or continuous culture reactor.

13. The process of claim 1, wherein the enzyme composition is in the form of a whole fermentation broth of a fungus.

14. The process of claim 1, wherein oxygen is introduced as an oxygen-containing gas, optionally air.

15. The process of claim 1, wherein the enzyme composition comprises a *Rasamsonia* enzyme.

16. The process of claim 9, wherein the enzymatic hydrolysis is conducted at a temperature of 55° C. or more.

17. The process of claim 11, wherein the dry matter content in the hydrolysis step is 14 to 33 wt %.

* * * * *